US006475782B1

(12) United States Patent
Escobedo et al.

(10) Patent No.: US 6,475,782 B1
(45) Date of Patent: *Nov. 5, 2002

(54) HUMAN PLATELET-DERIVED GROWTH FACTOR RECEPTOR

(75) Inventors: Jaime A. Escobedo; Lewis T. Williams, both of San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/451,693

(22) Filed: May 26, 1995

Related U.S. Application Data

(60) Division of application No. 08/240,294, filed on May 9, 1994, now Pat. No. 6,110,737, which is a continuation of application No. 08/031,082, filed on Mar. 15, 1993, now abandoned, which is a continuation of application No. 07/771,829, filed on Oct. 7, 1991, now abandoned, which is a continuation of application No. 07/309,322, filed on Feb. 10, 1989, now abandoned, which is a continuation-in-part of application No. 07/151,414, filed on Feb. 2, 1988, now abandoned.

(51) Int. Cl.[7] .......................... C12N 5/10; C07K 14/435; C07K 14/71; C07K 14/715
(52) U.S. Cl. ................... 435/325; 435/69.1; 435/320.1; 435/455; 530/300; 530/350
(58) Field of Search ................................ 530/350, 300; 435/240.2, 320.1, 172.3, 69.1, 325, 455; 935/70, 71

(56) References Cited

U.S. PATENT DOCUMENTS

| 4,766,073 A | 8/1988 | Murray et al. ............ 435/172.3 |
| 5,371,205 A | 12/1994 | Kelly et al. ................. 536/23.5 |

FOREIGN PATENT DOCUMENTS

| EP | 0 325 224 | 7/1989 | ............ C12N/15/00 |
| EP | 0 327 369 | 8/1989 | ............ C12N/15/00 |
| WO | 90/10013 | 9/1990 | ............ C07H/21/04 |

OTHER PUBLICATIONS

B Alberts et al (1983) Molecular Biology of the Cell, Garland Publishing, pp. 118–119, 177–179, 626–627.*
Bishayee et al., PNAS 83 : 6756–6760 (1986).*
Haynes et al., Nucleic Acids Res. 11(3) : 687–706 (1983).*
Peralta et al., Science 236 : 600–605 (1987).*
Yarden et al., Nature 323 : 226–232 (1986).*
Anderson et al., "Binding of SH2 Domains of Phospholipase $C_\gamma 1$, GAP, and Src to Activated Growth Factor Receptors," *Science*, 250:979–982 (1990).
Bell et al., "Effect of Platelet Factors on Migration of Cultured Bovine Aortic Endothelial and Smooth Muscle Cells," *Circulation Research*, 65(4):1057–1065 (1989).

Betsholtz et al., "Coexpression of a PDGF–like Growth Factor and PDGF Receptors in Human Osteosarcoma Cell Line: Implications for Autocrine Receptor Activation," *Cell*, 39:447–457 (1984).
Bishayee et al., "Ligand–induced Dimerization of the Platelet–derived Growth Factor Receptor," *J. Biol. Chem.*, 264(20):11699–11705 (1989).
Claesson–Welsh et al., "cDNA cloning and expression of a human platelet–derived growth factor (PDGF) receptor specific for B–chain–containing PDGF Molecules," *Mol. Cell. Biol.*, 8:3476–3486 (1988).
Claesson–Welsh et al., "Identification and Structural Analysis of the A Type Receptor for Platelet–derived Growth Factor" *J. Biol. Chem.*, 264(3):1742–1747, (1989).
Claesson–Welsh et al., "cDNA cloning and expression of the human A–type platelet–derived growth factor (PDGF) receptor establishes structural similarity to the B–type PDGF receptor," *Proc. Nat'l Acad. Sci. USA*, 86:4917–4921 (1989).
Coughlin et al., "Role of Phosphatidylinositol Kinase in PDGF Receptor Signal Transduction," *Science*, 243:1191–1194 (1989).
Daniel et al., "Purification of the platelet–derived growth factor receptor by using an anti–phosphotyrosine antibody," *Proc. Nat'l Acad. Sci. USA*, 82:2684–2687 (1985).
Daniel et al., "Biosynthetic and Glycosylation Dtudies of Cell Surface Platelet–derived Growth Factor Receptors," *J. Biol. Chem.*, 262(20):9778–9784 (1987).
Escobedo et al., "Role of Tyrosine Kinase and Membrane–Spanning Domains in Signal Transduction by the Platelet–Derived Growth Factor Receptor," *Mol. Cell. Biol.*, 8(12):5126–5131 (1988).
Escobedo et al., "Platelet–derived Growth Factor Receptors Expressed by cDNA Transfection Couple to a Diverse Group of Cellular Responses Associated with Cell Proliferation," *J. Biol. Chem.*, 263(3):1482–1487 (1988).
Escobedo et al., "A PDGF receptor domain essential for mitogenesis but not for many other responses to PDGF," *Nature*, 335:85–87 (1988).
Escobedo et al., "A Common PDGF Receptor Is Activated by Homodimeric A and B Forms of PDGF," *Science*, 240:1532–1534 (1988).

(List continued on next page.)

*Primary Examiner*—Scott D. Priebe
(74) *Attorney, Agent, or Firm*—Townsend and Townsend and Crew LLP

(57) ABSTRACT

A DNA sequence encoding human platelet-derived growth factor receptor (hPDGF-R) has now been isolated and sequenced. An expression construct comprising the sequence encodes a receptor that can be secreted or incorporated into the membrane of a mammalian cell. The incorporated receptor is functionally equivalent to the wild-type receptor, conferring a PDGF-sensitive mitogenic response on cells lacking the receptor. The construct can be used for enhancing PDGF response of cells, determining the regions involved in transducing the signal in response to PDGF binding, providing mutated analogs and evaluating drugs for their physiologic activity.

18 Claims, 26 Drawing Sheets

OTHER PUBLICATIONS

Felder et al., "Kinase Activity Controls the Sorting of the Epidermal Growth Factor Receptor within the Multivesicular Body," *Cell*, 61:623–634 (1990).

Giese et al., "The Role of Individual Cysteine Residues in the Structure and Function of the v–sis Gene Product," *Science*, 236:1315–1318 (1987).

Glenn et al., "Platelet–derived Growth Factor," *J. Biol. Chem.* 257(9):5172–5176 (1982).

Gronwald et al., "Cloning and expression of a cDNA coding for the human platelet–derived growth factor receptor: Evidence for more than one receptor class," *Proc. Nat'l Acad. Sci. USA*, 85:3435–3439 (1988).

Hart et al., "Synthesis, Phosphorylation, and Degradation of Multiple Forms of the Platelet–derived Growth Factor Receptor Studies Using a Monoclonal Antibody," *J. Biol. Chem.*, 262(22):10780–10785 (1987).

Hart et al., "Two classes of PDGF Receptor Recognize Different Isoforms of PDGF," *Science*, 240:1529–1531 (1988).

Hart et al., "Expression of Secreted Human Immunoglobulin/PDGF–Receptor Fusion Proteins Which Demonstrate High Affinity Ligand Binding," *Miami Winter Cancer Symposium* (1989).

Haynes et al., "Constitutive, long–term production of human interferons by hamster cells containing multiple copies of a cloned interferon gene," *Nucl. Acids Res.*, 11(3):687–706 (1983).

Heidaran et al., "Chimeric α– and β–Platelet–derived Growth Factor (PDGF) Receptors Define Three Immunoglobulin–like Domains of the α–PDGF Receptor That Determine PDGF–AA Binding Specificity," *J. Biol. Chem.*, 265(31):18741–18744 (1990).

Heldin et al., "Interaction of Platelet–derived Growth Factor with Its Fibroblast Receptor," *J. Biol. Chem.*, 257(8):4216–4221 (1982).

Heldin et al., "Binding of different dimeric forms of PDGF to human fibroblasts: evidence for two separate receptor types," *EMBO J.*, 7(5):1387–1393 (1988).

Heldin et al., "Dimerization of B–type Platelet–derived Growth Factor Receptors Occurs after Ligand Binding and Is Closely Associated with Receptor Kinase Activation," *J. Biol. Chem.*, 264(15):8905–8912 (1989).

Kaplan et al., "PDGF β–Receptor Stimulates Tyrosine Phosphorylation of GAP and Association of GAP with a Signaling Complex," *Cell*, 61:125–133 (1990).

Kazlauskas et al., "Different effects of homo– and heterodimers of patelet–derived growth factor A and B chains on human and mouse fibroblasts," *EMBO J.*, 7(12):3727–3735 (1988).

Keating et al., "Processing of the Platelet–derived Growth Factor Receptor," *J. Biol. Chem.*, 262(16):7932–7937 (1987).

Keating et al., "Autocrine Stimulation of Intracellular PDGF Receptors in v–sis–Transformed Cells," *Science*, 239:914–916 (1988).

Keating et al., "Ligand Activation Causes a Phosphorylation–dependent Change in Platelet–derived Growth Factor Receptor Conformation," *J. Biol. Chem.*, 263(26):12805–12808 (1988).

Keating et al., "Platelet–derived Growth Factor Receptor Inducibility Is Acquired Immediately after Translation and Does Not Require Glycosylation," *J. Biol. Chem.*, 264(16):9129–9132 (1989).

Kimball et al., "Epidermal Growth Factor (EGF) Binding to Membranes Immobilized in Microtiter Wells and Estimation of EGF–Related Transforming Growth Factor Activity," *Biochimica et Biophysica Acta*, 771:82–88 (1984).

Kornbluth et al., "Novel Tyrosine Kinase Identified by Phosphotyrosine Antibody Screening of cDNA Libraries," *Mol. Cell. Biol.*, 8(12):5541–5544 (1988).

Kypta et al., "Association between the PDGF Receptor and Members of the src Family of Tyrosine Kinases," *Cell*, 62:481–492 (1990).

Matsui et al., "Independent expression of human α or β platelet–derived growth factor receptor cDNAs in a naive hematopoietic cell leads to functional coupling with mitogenic and chemotactic signaling pathways," *Proc. Natl. Acad. Sci. USA*, 8:8314–8318 (1989).

Matsui et al., "Isolation of a Novel Receptor cDNAs Establishes the Existence of Two PDGF Receptor Genes," *Science*, 243:800–804 (1989).

Moran et al., "Src homology region 2 domains direct protein—protein interactions in signal transduction," *Proc. Nat'l Acad. Sci. USA*, 87:8622–8626 (1990).

Morrison et al., "Direct Activation of the Serine/Threonine Kinase Activity of Raf–1 through Tyrosine Phosphorylation by the PDGF β–Receptor," *Cell*, 58:649–657 (1989).

Morrison et al., "Platelet–Derived Growth Factor (PDGF) Dependent Association of Phospholipase C–γ with the PDGF Receptor Signaling Complex," *Mol. Cell. Biol.*, 10(5):2359–2366 (1990).

Nishibe et al., "Increase of the Catalytic Activity of Phospholipase C–γ1 by Tyrosine Phosphorylation," *Science*, 250:1253–1256 (1990).

Nister et al., "A Glioma–Derived PDGF A Chain Homodimer Has Different Functional Activities from a PDGF AB Heterodimer Purified from Human Platelets," *Cell*, 52:791–799 (1988).

Orchansky et al., "Phosphatidylinositol Linkage of a Truncated Form of the Platelet–derived Growth Factor Receptor," *J. Biol. Chem.*, 263(29):15159–15165.

Peralta et al., "Primary Structure and Biochemical Properties of an $M_2$ Muscarinic Receptor," *Science*, 236:600–605 (1987).

Qiu et al., "Primary structure of c–kit: relationship with the CSF–1/PDGF receptor kinase family—oncogenic activation of v–kit involves deletion of extracellular domain and C terminus," *EMBO J.*, 7(4):1003–1011 (1988).

Reid et al., "Two forms of the basic fibroblast growth factor receptor–like mRNA are expressed in the developing mouse brain," *Proc. Nat'l Acad. Sci. USA*, 87:1596–1600 (1990).

Ronnstrand et al., "Purification of the Receptor for Platelet-derived Growth Factor from Porcine Uterus," *J. Biol. Chem.*, 262(7):2929–2932 (1987).

Roussel et al., "Transforming potential of the c–fms proto–oncogene (CSF–1 receptor)," *Nature*, 325:549–552 (1987).

Ruta et al., "A novel protein tyrosine kinase gene whose expression is modulated during endothelial cell differentiation," *Oncogene*, 3:9–15 (1988).

Seifert et al., "Two Different Subunits Associate to Create Isoform–specific Platelet–derived Growth Factor Receptors," *J. Biol. Chem.*, 264(15):8771–8778 (1989).

Ullrich et al., "Signal Transduction by Receptors with Tyrosine Kinase Activity," *Cell*, 61:203–212 (1990).

van der Schaal et al., "An Enzyme–Linked Lectin Binding Assay for Quantitative Determination of Lectin Receptors," *Anal. Biochem.*, 140:48–55 (1984).

van Driel et al., "Stoichiometric Binding of Low Density Lipoprotein (LDL) Monoclonal Antibodies to LDL Receptors in a Solid Phase Assay," *J. Biol. Chem.*, 264(16):9533–9538 (1989).

Williams et al., "Platelet–derived growth factor binds specifically to receptors on vascular smooth muscle cells and the binding becomes nondissociable," *Proc. Nat'l Acad. Sci. USA*, 79:5867–5870 (1982).

Williams et al., "Platelet–derived Growth Factor Receptors Form a High Affinity State in Membrane Preparations," *J. Biol. Chem.*, 259(8):5287–5294 (1984).

Williams et al., "PDGF Receptors: Structural and Functional Studies," *Miami Winter Symposium*, 4:168–171 (1986).

Williams et al., "The Stimulation of Paracrine and Autocrine Mitogenic Pathways by the Platelet–Derived Growth Factor Receptor," *J. Cell. Physiol. Supp.*, 5:27–30 (1987).

Williams et al., "Signal Transduction by the Platelet-–Derived Growth Factor Receptor," *CSH Symp. Quant. Biol.*, 53:455–465 (1988).

Williams et al., "The Immunoglobulin Superfamily—Domains for Cell Surface Recognition," *Ann. Rev. Immunology*, 6:381–405 (1988).

Williams, "Stimulation of Paracrine and Autocrine Pathways of Cell Proliferation by Platelet–Derived Growth Factor," *Clinical Research*, 36:5–10 (1988).

Williams, "Signal Transduction by the Platelet–Derived Growth Factor Receptopr Involves Association of the Receptor with Cytoplasmic Molecules," *Clinical Research*, 37:564–568 (1989).

Williams, "Signal Transduction by the Platelet–Derived Growth Factor Receptor," *Science*, 243:1564–1570 (1989).

Yarden et al., "Structure of the receptor for platelet–derived growth factor helps define a family of closely related growth factor receptors," *Nature*, 323:226–232 (1986).

Yarden et al., "Growth Factor Receptor Tyrosine Kinases," *Ann. Rev. Biochem.*, 57:443–478 (1988).

\* cited by examiner

Fig. 1A

```
cgctggctgc tggcagcaga gtgactgccc gccctatctg ggacccagga tcgctctgtg   60
agcaacttgg agccagagag gagatcaaca aggaggagga gagagccggc ccctcagccc  120
tgctgcccag cagcagcctg tgctcgccct gcccaacgca gacagccaga cccagggcgg  180
cccctctggc ggctctgctc ctccgaagat gcttggggag tgaggcgaca tggggccgct  240
cctctcccct acagcagccc ccttcctcca tccctctgtt ctcctgagcc ttcaggagcc  300
tgcaccagtc ctgcctgtcc ttctactcag ctgttaccca ctctgggacc agcagtcttt  360
ctgataactg ggagagggca gtaaggagga cttcctggag ggggtgactg tccagagcct  420
ggaactgtgc ccacaccaga agcaaggaca agccatcagc cc atg cgg ctt ccg     474
                                             Met Arg Leu Pro
                                              -32 ggt gcg atg cca gct ctg gcc ctc aaa ggc gag ctg ttg ctg tct         522
Gly Ala Met Pro Ala Leu Ala Leu Lys Gly Glu Leu Leu Leu Ser
-28                     -23                     -18          -13 ctc ctg tta ctt ctg gaa cca cag atc tct cag ggc ctg gtc gtc aca     570
Leu Leu Leu Leu Leu Glu Pro Gln Ile Ser Gln Gly Leu Val Val Thr
         -8                      -3                       3
```

Fig. 1B

```
ccc ccg ggg cca gag ctt gtc ctc aat gtc tcc agc acc ttc gtt ctg    618
Pro Pro Gly Pro Glu Leu Val Leu Asn Val Ser Ser Thr Phe Val Leu
                8                    13                    18 acc tgc tcg ggt tca gct ccg gtg gtg tgg gaa cgg atg tcc cag gag    666
Thr Cys Ser Gly Ser Ala Pro Val Val Trp Glu Arg Met Ser Gln Glu
         23                    28                    33 ccc cca cag gaa atg gcc aag gcc cag gat ggc acc ttc tcc agc gtg    714
Pro Pro Gln Glu Met Ala Lys Ala Gln Asp Gly Thr Phe Ser Ser Val
         38                    43                    48 ctc aca ctg acc aac ctc act ggg cta gac acg gga gaa tac ttt tgc    762
Leu Thr Leu Thr Asn Leu Thr Gly Leu Asp Thr Gly Glu Tyr Phe Cys
 53                    58                    63                 68 acc cac aat gac tcc cgt gga ctg gag acc gat gag cgg aaa cgg ctc    810
Thr His Asn Asp Ser Arg Gly Leu Glu Thr Asp Glu Arg Lys Arg Leu
         73                    78                    83 tac atc ttt gtg cca gat ccc acc gtg ggc ttc ctc cct aat gat gcc    858
Tyr Ile Phe Val Pro Asp Pro Thr Val Gly Phe Leu Pro Asn Asp Ala
         88                    93                    98
```

Fig. 1C

```
gag gaa cta ttc atc ttt ctc acg gaa ata act gag atc acc att cca    906
Glu Glu Leu Phe Ile Phe Leu Thr Glu Ile Thr Glu Ile Thr Ile Pro
            103                 108                 113 tgc cga gta aca gac cca cag ctg gtg gtg aca ctg cac gag aag aaa    954
Cys Arg Val Thr Asp Pro Gln Leu Val Val Thr Leu His Glu Lys Lys
        118                 123                 128 ggg gac gtt gca ctg cct gtc ccc tat gat cac caa cgt ggc ttt tct   1002
Gly Asp Val Ala Leu Pro Val Pro Tyr Asp His Gln Arg Gly Phe Ser
            133                 138                 143 ggt atc ttt gag gac aga agc tac atc tgc aaa acc acc att ggg gac   1050
Gly Ile Phe Glu Asp Arg Ser Tyr Ile Cys Lys Thr Thr Ile Gly Asp
            153                 158                 163 agg gag gtg gat tct gat gcc tac tat gtc tac aga ctc cag gtg tca   1098
Arg Glu Val Asp Ser Asp Ala Tyr Tyr Val Tyr Arg Leu Gln Val Ser
            168                 173                 178 tcc atc aac gtc tct gtg aac gca gtg cag act gtg cgc cag ggt       1146
Ser Ile Asn Val Ser Val Asn Ala Val Gln Thr Val Arg Gln Gly
            183                 188                 193
```

Fig. 1D

```
gag aac atc acc ctc atg tgc att gtg atc ggg aat gag gtg gtc aac    1194
Glu Asn Ile Thr Leu Met Cys Ile Val Ile Gly Asn Glu Val Val Asn
         198                 203                 208 ttc gag tgg aca tac ccc cgc aaa gaa agt ggg cgg ctg gtg gag ccg    1242
Phe Glu Trp Thr Tyr Pro Arg Lys Glu Ser Gly Arg Leu Val Glu Pro
 213                 218                 223                 228 gtg act gac ttc ctc ttg gat atg cct tac cac atc cgc tcc atc ctg    1290
Val Thr Asp Phe Leu Leu Asp Met Pro Tyr His Ile Arg Ser Ile Leu
         233                 238                 243 cac atc ccc agt gcc gag tta gaa gac tcg ggg acc tac acc tgc aat    1338
His Ile Pro Ser Ala Glu Leu Glu Asp Ser Gly Thr Tyr Thr Cys Asn
 248                 253                 258 gtg acg gag agt gtg aat gac cat cag gat gaa aag gcc atc aac atc    1386
Val Thr Glu Ser Val Asn Asp His Gln Asp Glu Lys Ala Ile Asn Ile
         263                 268                 273 acc gtt gag agc ggc tac gtg cgg ctc ctg gga gag gtg ggc aca        1434
Thr Val Glu Ser Gly Tyr Val Arg Leu Leu Gly Glu Val Gly Thr
 278                 283                 288
```

Fig. 1E

```
cta caa ttt gct gag ctg cat cgg agc cgg aca ctg cag gta gtg ttc    1482
Leu Gln Phe Ala Glu Leu His Arg Ser Arg Thr Leu Gln Val Val Phe
293             298                 303                 308 gag gcc tac cca ccg ccc act gtc ctg tgg ttc aaa gac aac cgc acc    1530
Glu Ala Tyr Pro Pro Pro Thr Val Leu Trp Phe Lys Asp Asn Arg Thr
    313                 318                 323 ctg ggc gac tcc agc gct ggc gaa atc gcc ctg gcc ctg tcc acg cgc aac gtg  1578
Leu Gly Asp Ser Ser Ala Gly Glu Ile Ala Leu Ala Leu Ser Thr Arg Asn Val
        328                 333                 338 tcg gag acc cgg tat gtg tca gag ctg aca ctg gtt cgc gtg aag gtg    1626
Ser Glu Thr Arg Tyr Val Ser Glu Leu Thr Leu Val Arg Val Lys Val
343                 348                 353 gca gag gct cgc cac tac acc atg cgg gcc ttc cat gag gat gct gag    1674
Ala Glu Ala Arg His Tyr Thr Met Arg Ala Phe His Glu Asp Ala Glu
    358                 363                 368 gtc cag ctc tcc ttc cag cta cag atc aat gtc cct gtc cga gtg ctg    1722
Val Gln Leu Ser Phe Gln Leu Gln Ile Asn Val Pro Val Arg Val Leu
373                 378                 383                 388
```

Fig. 1F

```
gag cta agt gag agc cac cct gac agt ggg gaa cag aca gtc cgc tgt      1770
Glu Leu Ser Glu Ser His Pro Asp Ser Gly Glu Gln Thr Val Arg Cys
            393                 398                 403 cgt ggc cgg ggc atg ccc cag ccg aac atc atc tgg tct gcc aga           1818
Arg Gly Arg Gly Met Pro Gln Pro Asn Ile Ile Trp Ser Ala Cys Arg
            408                 413                 418 gac ctc aaa agg tgt cca cgt gag ctg ccg ccc acg ctg ggg aac           1866
Asp Leu Lys Arg Cys Pro Arg Glu Leu Pro Pro Thr Leu Gly Asn
            423                 428                 433 agt tcc gaa gag gag agc cag ctg gag act aac gtg acg tac tgg gag       1914
Ser Ser Glu Glu Glu Ser Gln Leu Glu Thr Asn Val Thr Tyr Trp Glu
            438                 443                 448 gag gag cag cag gag ttt gag gtg agc aca ctg cgt ctg cag cac gtg       1962
Glu Glu Gln Gln Glu Phe Glu Val Ser Thr Leu Arg Leu Gln His Val
            453                 458                 463                 468 gat cgg cca ctg tcg gtg cgc tgc acg cgc aac gct gtg ggc cag           2010
Asp Arg Pro Leu Ser Val Arg Cys Thr Leu Arg Asn Ala Val Gly Gln
            473                 478                 483
```

Fig. 1G

```
gac acg cag gag gtc atc gtg gtg cca cac tcc ttg ccc ttt aag gtg    2058
Asp Thr Gln Glu Val Ile Val Val Pro His Ser Leu Pro Phe Lys Val
            488                 493                 498 gtg gtg atc tca gcc atc ctg gcc atc tca ctg gtg gtg ctc acc atc atc tcc    2106
Val Val Ile Ser Ala Ile Leu Ala Ile Ser Leu Val Val Leu Thr Ile Ile Ser
            503                 508                 513 ctt atc atc ctc atg ctt tgg cag aag cca cgt tac gag atc    2154
Leu Ile Ile Leu Met Leu Trp Gln Lys Pro Arg Tyr Glu Ile
            518                 523                 528 cga tgg aag gtg att gag tct gtg agc tct gac ggc cat gag tac atc    2202
Arg Trp Lys Val Ile Glu Ser Val Ser Ser Asp Gly His Glu Tyr Ile
            533                 538                 543                 548 tac gtg gac ccc atg cag ctg ccc tat gac tcc acg tgg gag ctg ccg    2250
Tyr Val Asp Pro Met Gln Leu Pro Tyr Asp Ser Thr Trp Glu Leu Pro
            553                 558                 563 cgg gac cag ctt gtg ctg gga cgc acc ctc ggc tct ggg gcc ttt ggg    2298
Arg Asp Gln Leu Val Leu Gly Arg Thr Leu Gly Ser Gly Ala Phe Gly
            568                 573                 578
```

Fig. 1H

```
cag gtg gtg gag gcc acg gct cat ggc ctg agc cat tct cag gcc acg    2346
Gln Val Val Glu Ala Thr Ala His Gly Leu Ser His Ser Gln Ala Thr
583                         588                         593 atg aaa gtg gcc gtc aag atg gtc ctt aaa tcc aca gcc cgc agc agt gag    2394
Met Lys Val Ala Val Lys Met Val Leu Lys Ser Thr Ala Arg Ser Ser Glu
        598                         603                         608 aag caa gcc ctt atg tcg gag ctg aag ctg aag atc atg agt cac ctt ggg ccc    2442
Lys Gln Ala Leu Met Ser Glu Leu Lys Leu Lys Ile Met Ser His Leu Gly Pro
613                         618                         623                         628 cac ctg aac gtc gtc aac ctg ttg ggg gcc tgc acc aaa gga gga ccc    2490
His Leu Asn Val Val Asn Leu Leu Gly Ala Cys Thr Lys Gly Gly Pro
633                         638                         643 atc tat atc atc act gag tac tgc cgc tac gga gac ctg gtg gac tac    2538
Ile Tyr Ile Ile Thr Glu Tyr Cys Arg Tyr Gly Asp Leu Val Asp Tyr
648                         653                         658 ctg cac cgc aac aaa cac acc ttc ctg cag cac cac tcc gac aag cgc    2586
Leu His Arg Asn Lys His Thr Phe Leu Gln His His Ser Asp Lys Arg
663                         668                         673
```

Fig. 1I

```
cgc ccg agc gcg gag ctc tac agc aat gct ctg ccc gtt ggg gtc    2634
Arg Pro Ser Ala Glu Leu Tyr Ser Asn Ala Leu Pro Val Gly Val
678                     683                 688 ccc ctg ccc agc cat gtg tcc ttg acc ggg gag agc gac ggt ggc tac    2682
Pro Leu Pro Ser His Val Ser Leu Thr Gly Glu Ser Asp Gly Gly Tyr
693                     698                 703                 708 atg gac atg agc aag gac gag tcg gtg gac tat gtg ccc atg ctg gac    2730
Met Asp Met Ser Lys Asp Glu Ser Val Asp Tyr Val Pro Met Leu Asp
713                     718                 723 atg aaa gga gac gtc aaa tat gca gac atc gag tcc aac tac atg    2778
Met Lys Gly Asp Val Lys Tyr Ala Asp Ile Glu Ser Asn Tyr Met
728                     733                 738 gcg cct tac gat aac tac gtt ccc tct gcc cct gag agg acc tgc cga    2826
Ala Pro Tyr Asp Asn Tyr Val Pro Ser Ala Pro Glu Arg Thr Cys Arg
743                     748                 753 gca act ttg atc aac gag tct cca gtg cta agc tac atg gac ctc gtg    2874
Ala Thr Leu Ile Asn Glu Ser Pro Val Leu Ser Tyr Met Asp Leu Val
758                     763                 768
```

Fig. 1J

```
ggc ttc agc tac cag gtg gcc aat ggc atg gag ttt ctg gcc tcc aag     2922
Gly Phe Ser Tyr Gln Val Ala Asn Gly Met Glu Phe Leu Ala Ser Lys
773                     778                     783                     788 aac tgc gtc cac aga gac ctg gcg gct agg aac gtg ctc atc tgt gaa     2970
Asn Cys Val His Arg Asp Leu Ala Ala Arg Asn Val Leu Ile Cys Glu
        793                     798                     803 ggc aag ctg gtc aag atc tgt gac ttt ggc ctg gct cga gac atc atg     3018
Gly Lys Leu Val Lys Ile Cys Asp Phe Gly Leu Ala Arg Asp Ile Met
        808                     813                     818 cgg gcc tcg aat tac atc tcc aaa ggc agc acc ttt cct tta aag         3066
Arg Ala Ser Asn Tyr Ile Ser Lys Gly Ser Thr Phe Pro Leu Lys
        823                     828                     833 tgg atg gct ccg gag agc atc ttc aac agc ctc tac acc acc ctg agc     3114
Trp Met Ala Pro Glu Ser Ile Phe Asn Ser Leu Tyr Thr Thr Leu Ser
838                     843                     848 gac gtg tgg tcc ttc ggg atc ctg ctc tgg gag atc ttc acc ttg ggt     3162
Asp Val Trp Ser Phe Gly Ile Leu Leu Trp Glu Ile Phe Thr Leu Gly
853                     858                     863                     868
```

Fig. 1K

```
ggc acc cct tac cca gag ctg ccc atg aac gag cag ttc tac aat gcc    3210
Gly Thr Pro Tyr Pro Glu Leu Pro Met Asn Glu Gln Phe Tyr Asn Ala
873                                 878                        883 atc aaa cgg ggt tac cgc atg gcc cag cct gcc cat gcc tcc gac gag    3258
Ile Lys Arg Gly Tyr Arg Met Ala Gln Pro Ala His Ala Ser Asp Glu
        888                         893                        898 atc tat gag atc atg cag aag tgc tgg gaa gag aag ttt gag att cgg    3306
Ile Tyr Glu Ile Met Gln Lys Cys Trp Glu Glu Lys Phe Glu Ile Arg
        903                         908                    913 ccc ccc ttc tcc cag ctg gtg ctg ctt ctc gag aga ctg ttg ggc gaa    3354
Pro Pro Phe Ser Gln Leu Val Leu Leu Leu Glu Arg Leu Leu Gly Glu
918                         923                         928 ggt tac aaa aag aag tac cag gtg cag gat gag gag ttt ctg agg agt    3402
Gly Tyr Lys Lys Lys Tyr Gln Val Gln Asp Glu Glu Phe Leu Arg Ser
933                         938                     943        948 gac cac cca gcc atc ctt cgg tcc cag gcc cgc ttg cct ggg ttc cat    3450
Asp His Pro Ala Ile Leu Arg Ser Gln Ala Arg Leu Pro Gly Phe His
        953                         958                        963
```

Fig. 1L

```
ggc ctc cga tct ccc ctg gac acc agc tcc gtc ctc tat act gcc gtg    3498
Gly Leu Arg Ser Pro Leu Asp Thr Ser Val Leu Tyr Thr Ala Val
            968                 973                 978 cag ccc aat gag ggt gac aac gac tat atc atc ccc ctg cct gac ccc    3546
Gln Pro Asn Glu Gly Asp Asn Asp Tyr Ile Ile Pro Leu Pro Asp Pro
            983                 988                 993 aaa ccc gag gtt gct gac gag ggc cca ctg gag ggt tcc ccc agc cta    3594
Lys Pro Glu Val Ala Asp Glu Gly Pro Leu Glu Gly Ser Pro Ser Leu
            998                1003                1008 gcc agc tcc acc ctg aat gaa gtc aac acc tcc tca acc atc tcc tgt Cys    3642
Ala Ser Ser Thr Leu Asn Glu Val Asn Thr Ser Thr Ile Ser Cys
    1013                1018                1023                1028 gac agc ccc gag ccc cag gac gaa cca gag ccc gag ccc cag ctt    3690
Asp Ser Pro Glu Pro Gln Asp Glu Pro Glu Pro Glu Pro Gln Leu
            1033                1038                1043 gag ctc cag gtg gag ccg gag cca gag ctg gaa cag ttg ccg gat tcg    3738
Glu Leu Gln Val Glu Pro Glu Pro Glu Leu Glu Gln Leu Pro Asp Ser
            1048                1053                1058
```

Fig 1M

```
ggg tgc cct gcg cct cgg gct gaa gca gag gat agc ttc ctg    3780
Gly Cys Pro Ala Pro Arg Ala Glu Ala Glu Asp Ser Phe Leu
    1063                1068                1073 tagggggctg gcccctaccc tgccctgcct gaagctcccc cctgccagc acccagcatc    3840
tcctggcctg gcctgaccgg gcttcctgtc agccaggctg cccttatcag ctgtcccctt    3900
ctggaagctt tctgctcctg acgtgttgtg cccaaaccc tggggctggc ttaggaggca    3960
agaaaactgc aggggccgtg accagccctc tgcctccagg gaggccaact gactctgagc    4020
cagggttccc ccagggaact cagtttttccc atatgtaaaa acaggtgggg tgggaaagtt aggcttgatg    4080
acccagaatc taggattctc tccctggctg acaggtgggg taactttttt agaccgaatc cctccctggg    4140
aagattcttg gagttactga ggtgtaaat ctcgacttta ctgttcagcc agctaccct    4200
caaggaatca tagctctctc ctcgacttta tccacccagg agctagggaa gagaccctag    4260
cctcccctggc tgctggctga gctagggcct agccttgagc agtgttgcct catccagaag    4320
aagccagtct cctccctatg atggccagta aatgcgttcc ctggcccgag ctggtctggg    4380
gccattaggc agcctaatta atgctggagg ctgagccaag tacaggacac ccccagcctg    4440
```

Fig. 1N

```
cagcccttgc ccagggcact tggagcacac gcaccatagc aagtcctgtg tccctgtcct 4500
tcaggcccat cagtcctggg gctttttctt tatcaccctc agtcttaatc catccaccag 4560
agtctagaag gccagacggg cccgcatct gtgatgagaa tgtaaatgtg ccagtgtgga 4620
gtggccacgt gtgtgtgcca gtatatggcc ctggctctgc attggacctg ctatgaggct 4680
ttggaggaat ccctcaccct cagtttcccc cagtttcccc ttcaaaaaat gaataagtcg 4740
gacttattaa ctctgatgcc ttgccagcac taacattcta gagtattcca ggtggttgca 4800
catttgtcca gatgaagcaa ggccatatac cctaaacttc catcctgggg gtcagctggg 4860
ctcctgggag attccagatc acacatcaca ctctggggac tcaggaacca tgcccctcc 4920
ccaggcccc agcaagtctc aagaacacag ctgcacaggc cttgacttag agtgacagcc 4980
ggtgtcctgg aaagccccca gcagctgccc caggacatgg gaagaccacg ggacctcttt 5040
cactacccac gatgacctcc gggggtatcc tgggcaaaag ggacaaagag ggcaaatgag 5100
atcacctcct gcagccacc actccagcac ctgtgccgag gtctgcgtcg aagacagaat 5160
ggacagtgag gacagttatg tcttggaaaa gacaagaagc ctcagagtgg gtaccccaag 5220
```

Fig. 10

```
aaggatgtga gaggtgggcg ctttggaggt ttgcccctca cccaccagct gccccatccc 5280
tgaggcagcg ctccatgggg gtatggtttt gtcactgccc agacctagca gtgacatctc 5340
attgtcccca gcccagtggg cattggaggt gccaggggag tcagggttgt agccaagacg 5400
cccgcacggg gagggttggg aaggggggtgc aggaagctca accccctctgg caccaaccct 5460
gcattgcagt tggcacctta cttccctggg atccccagag ttggtccaag gagggagagt 5520
gggttctcaa tacggtacca aagatataat cacctaggtt tacaaatatt tttaggactc 5580
acgttaactc acatttatac agcagaaatg ctatttgtg atgctgttaa gttttctat 5640
ctgtgtactt ttttttaagg gaaagatttt aatattaaac ctggtcttct caaaaaaaaa 5700
aaaaaaaaa aaaaaaaaa                                                5720
```

Fig. 2A

```
a aat gaa aag gtt gtg cag ctg aat tca tcc ttt tct ctg aga tgc ttt   49
  Asn Glu Lys Val Val Gln Leu Asn Ser Ser Phe Ser Leu Arg Cys Phe
   1               5                  10                  15 ggg gag agt gaa gtg agc tgg cag tac ccc atg tct gaa gag agc        97
Gly Glu Ser Glu Val Ser Trp Gln Tyr Pro Met Ser Glu Glu Ser
                    20                  25                  30 tcc gat gtg gaa atc aga aat gaa gaa aac agc ggc ctt tct gtg       145
Ser Asp Val Glu Ile Arg Asn Glu Glu Asn Ser Gly Leu Ser Val
                35                  40                  45 acg gtc ttg gaa gtg agc agt gcc tcg gcg gcc cac aca ggg ttg tac   193
Thr Val Leu Glu Val Ser Ser Ala Ser Ala Ala His Thr Gly Leu Tyr
            50                  55                  60 act tgc tat tac aac cac act cag aca gaa gag aat gag ctt gaa ggc   241
Thr Cys Tyr Tyr Asn His Thr Gln Thr Glu Glu Asn Glu Leu Glu Gly
65                  70                  75                  80 agg cac att tac atc tat gtg cca gac gta gcc ttt gta cct           289
Arg His Ile Tyr Ile Tyr Val Pro Asp Val Ala Phe Val Pro
                85                  90                  95
```

Fig. 2B

```
cta gga atg acg gat tat tta gtc atc gtg gag gat gat gat tct gcc    337
Leu Gly Met Thr Asp Tyr Leu Val Ile Val Glu Asp Asp Asp Ser Ala
         100                 105                 110 att ata cct tgt cgc aca act gat ccc gag act cct gta acc tta cac    385
Ile Ile Pro Cys Arg Thr Thr Asp Pro Glu Thr Pro Val Thr Leu His
         115                 120                 125 aac agt gag ggg gtg gta cct gcc tcc tac gac agc aga cag ggc ttt    433
Asn Ser Glu Gly Val Val Pro Ala Ser Tyr Asp Ser Arg Gln Gly Phe
         130                 135                 140 aat ggg acc ttc act gta ggg ccc tat atc tgt gag gcc acc gtc aaa    481
Asn Gly Thr Phe Thr Val Gly Pro Tyr Ile Cys Glu Ala Thr Val Lys
         145                 150                 155                 160 gga aag ttc cag acc atc cca ttt aat gtt tat gct tta aaa gca        529
Gly Lys Phe Gln Thr Ile Pro Phe Asn Val Tyr Ala Leu Lys Ala
         165                 170                 175 aca tca gag ctg gat cta gaa atg gaa gct ctt aaa acc gtg tat aag    577
Thr Ser Glu Leu Asp Leu Glu Met Glu Ala Leu Lys Thr Val Tyr Lys
         180                 185                 190
```

Fig. 2C

```
tca ggg gaa acg att gtg gtc acc tgt gct gtt ttt aac aat gag gtg    625
Ser Gly Glu Thr Ile Val Val Thr Cys Ala Val Phe Asn Asn Glu Val
195                 200                 205 gtt gac ctt caa tgg act tac cct tac ccg gaa gtg aaa ggc atc        673
Val Asp Leu Gln Trp Thr Tyr Pro Tyr Pro Glu Val Lys Gly Ile
210                 215                 220 aca atg ctg gaa gaa atc aaa gtc cca tcc atc aaa ttg gtg tac act    721
Thr Met Leu Glu Glu Ile Lys Val Pro Ser Ile Lys Leu Val Tyr Thr
225                 230                 235                 240 ttg acg gtc ccc gag gcc acg gtg aaa gac agt gga gat tac gaa tgt    769
Leu Thr Val Pro Glu Ala Thr Val Lys Asp Ser Gly Asp Tyr Glu Cys
245                 250                 255 gct gcc cgc cag gct acc agg gag gtc aaa gaa atg aag aaa gtc act    817
Ala Ala Arg Gln Ala Thr Arg Glu Val Lys Glu Met Lys Lys Val Thr
260                 265                 270 att tct gtc cat gag aaa ggt ttc att gaa atc aaa ccc acc ttc agc    865
Ile Ser Val His Glu Lys Gly Phe Ile Glu Ile Lys Pro Thr Phe Ser
275                 280                 285
```

Fig. 2D

```
cag ttg gaa gct gtc aac ctg cat gaa gtc aaa cat ttt gtt gta gag    913
Gln Leu Glu Ala Val Asn Leu His Glu Val Lys His Phe Val Val Glu
    290                 295                 300 gtg cgg gcc tac cca cct ccc agg ata tcc tgg ctg aaa aac aat ctg    961
Val Arg Ala Tyr Pro Pro Pro Arg Ile Ser Trp Leu Lys Asn Asn Leu
305                 310                 315                 320 act ctg att gaa aat ctc act gag atc acc act gat gtg gaa aag att   1009
Thr Leu Ile Glu Asn Leu Thr Glu Ile Thr Thr Asp Val Glu Lys Ile
                325                 330                 335 cag gaa ata agg tat cga agc aaa tta aag ctg atc cgt gct aac caa   1057
Gln Glu Ile Arg Tyr Arg Ser Lys Leu Lys Leu Ile Arg Ala Asn Gln
            340                 345                 350 gaa gac agt ggc cat tat act att gta gct caa aat gaa gat gct gtg   1105
Glu Asp Ser Gly His Tyr Thr Ile Val Ala Gln Asn Glu Asp Ala Val
        355                 360                 365 aag agc tat act ttt gaa ctg tta act caa gtt cct tca tcc att ctg   1153
Lys Ser Tyr Thr Phe Glu Leu Leu Thr Gln Val Pro Ser Ser Ile Leu
    370                 375                 380
```

Fig. 2E

```
gac ttg gtc gat gat cac cat ggc tca act ggg gga cag acg gtg agg    1201
Asp Leu Val Asp Asp His His Gly Ser Thr Gly Gly Gln Thr Val Arg
385                 390                 395                 400 tgc aca gct gaa ggc acg ccg ctt cct gat att gag tgg atg ata tgc    1249
Cys Thr Ala Glu Gly Thr Pro Leu Pro Asp Ile Glu Trp Met Ile Cys
        405                 410                 415 aaa gat att aag aaa tgt aat gaa act aat gaa act att ttg gcc        1297
Lys Asp Ile Lys Lys Cys Asn Glu Thr Asn Glu Thr Ile Leu Ala
420                 425                 430 aac aat gtc tca aac atc acg gag atc cac tcc cga gac agg agt        1345
Asn Asn Val Ser Asn Ile Thr Glu Ile His Ser Arg Asp Arg Ser
435                 440                 445 acc gtg gag ggc cgt gtg act gtg act ttc gcc aaa gtg gag acc atc gcc 1393
Thr Val Glu Gly Arg Val Thr Val Thr Phe Ala Lys Val Glu Thr Ile Ala
450                 455                 460 gtg cga tgc ctg gct aag aat ctc ctt gga gct gag aac cga gag ctg    1441
Val Arg Cys Leu Ala Lys Asn Leu Leu Gly Ala Glu Asn Arg Glu Leu
465                 470                 475                 480
```

Fig. 2F

```
aag ctg gtg gct ccc acc ctg cgt tct gaa ctc acg gtg gct gca      1489
Lys Leu Val Ala Pro Thr Leu Arg Ser Glu Leu Thr Val Ala Ala
                485                 490                 495 gtc ctg gtg ctg ttg gtg att gtg atc tca ctt att gtc ctg gtt      1537
Val Leu Val Leu Leu Val Ile Val Ile Ser Leu Ile Val Leu Val
            500                 505                 510 gtc att tgg aaa cag aaa ccg agg tat gaa att cgc tgg agg gtc att  1585
Val Ile Trp Lys Gln Lys Pro Arg Tyr Glu Ile Arg Trp Arg Val Ile
        515                 520                 525 gaa tca atc agc ccg gat gga cat gaa tat att tat gtg gac ccg atg  1633
Glu Ser Ile Ser Pro Asp Gly His Glu Tyr Ile Tyr Val Asp Pro Met
    530                 535                 540 cag ctg cct tat gac tca aga tgg gag ttt cca aga gat gga cta gtg  1681
Gln Leu Pro Tyr Asp Ser Arg Trp Glu Phe Pro Arg Asp Gly Leu Val
545                 550                 555                 560 ctt ggt cgg gtc ttg ggg tct gga gcg ttt ggg aag gtg gtt gaa gga  1729
Leu Gly Arg Val Leu Gly Ser Gly Ala Phe Gly Lys Val Val Glu Gly
            565                 570                 575
```

Fig. 2G

```
aca gcc tat gga tta agc cgg tcc caa cct gtc atg aaa gtt gca gtg    1777
Thr Ala Tyr Gly Leu Ser Arg Ser Gln Pro Val Met Lys Val Ala Val
                580                 585                 590 aac atg cta aaa ccc acg gcc aga gcc agt gaa aaa caa gct ctc atg    1825
Asn Met Leu Lys Pro Thr Ala Arg Ser Ser Glu Lys Gln Ala Leu Met
            595                 600                 605 tct gaa ctg aag ata atg act cac ctg ggg cca cat ttg aac att gta    1873
Ser Glu Leu Lys Ile Met Thr His Leu Gly Pro His Leu Asn Ile Val
        610                 615                 620 aac ttg ctg gga gcc tgc acc aag tca ggc ccc att tac atc atc aca    1921
Asn Leu Leu Gly Ala Cys Thr Lys Ser Gly Pro Ile Tyr Ile Ile Thr
    625                 630                 635                 640 gag tat tgc ttc tat gga ggt gly asp leu val aac tat ttg cat aag aat agg    1969
Glu Tyr Cys Phe Tyr Gly Asp Leu Val Asn Tyr Leu His Lys Asn Arg
645                 650                 655 gat agc ttc ctg agc cac cac cca gag aag cca aag aaa gag ctg gat    2017
Asp Ser Phe Leu Ser His His Pro Glu Lys Pro Lys Lys Glu Leu Asp
    660                 665                 670
```

Fig. 2H

```
atc ttt gga ttg aac cct gct gat gaa agc aca cgg agc tat gtt att    2065
Ile Phe Gly Leu Asn Pro Ala Asp Glu Ser Thr Arg Ser Tyr Val Ile
675                 680                 685 tta tct ttt gaa aac aat ggt gac tac atg gac atg aag cag gct gat    2113
Leu Ser Phe Glu Asn Asn Gly Asp Tyr Met Asp Met Lys Gln Ala Asp
        690                 695                 700 act aca cag tat gtc ccc atg cta gaa agg aaa gag gtt tct aaa tat    2161
Thr Thr Gln Tyr Val Pro Met Leu Glu Arg Lys Glu Val Ser Lys Tyr
705                 710                 715                 720 tcc gac gtc cag aga tca gat cgt cca gcc tca tat aag aag            2209
Ser Asp Val Gln Arg Ser Asp Arg Pro Ala Ser Tyr Lys Lys
            725                 730                 735 aaa tct atg tta gac tca gaa gtc aaa aac ctc ctt tca gat gat aac    2257
Lys Ser Met Leu Asp Ser Glu Val Lys Asn Leu Ser Asp Asp Asn
                740                 745                 750 tca gaa ggc ctt act tta ttg gat ttg ttg agc ttc acc tat caa gtt    2305
Ser Glu Gly Leu Thr Leu Leu Asp Leu Leu Ser Phe Thr Tyr Gln Val
        755                 760                 765
```

Fig. 2I

| | | | | | | | | | | | | | | | |
|---|---|---|---|---|---|---|---|---|---|---|---|---|---|---|---|
| gcc | cga | gga | atg | gag | ttt | ttg | gct | tca | aaa | aat | tgt | gtc | cac | cgt | gat |
| Ala | Arg | Gly | Met | Glu | Phe | Leu | Ala | Ser | Lys | Asn | Cys | Val | His | Arg | Asp |
| 770 | | | | | 775 | | | | | 780 | | | | | 2353 | ctg gct gct cgc aac gtc ctc ctg gca caa gga aaa att gtg aag atc
Leu Ala Ala Arg Asn Val Leu Leu Ala Gln Gly Lys Ile Val Lys Ile
785          790          795          800    2401 tgt gac ttt ggc ctg gcc aga gac atc atg cat gat tcg ttc tat gtg
Cys Asp Phe Gly Leu Ala Arg Asp Ile Met His Asp Ser Phe Tyr Val
        805          810          815    2449 tcg aaa ggc agt acc ttt ctg ccc gtg aag tgg atg gct cct gag agc
Ser Lys Gly Ser Thr Phe Leu Pro Val Lys Trp Met Ala Pro Glu Ser
        820          825          830    2497 atc ttt gac aac ctc tac acc aca ctg agt gat gtc tgg tct tat ggc
Ile Phe Asp Asn Leu Tyr Thr Thr Leu Ser Asp Val Trp Ser Tyr Gly
835          840          845    2545 att ctg ctc tgg gag atc ttt tcc ctt ggt ggc acc cct tac ccc ggc
Ile Leu Leu Trp Glu Ile Phe Ser Leu Gly Gly Thr Pro Tyr Pro Gly
850          855          860    2593

Fig. 2J

```
atg atg gtg gat tct act ttc tac aat aag atc aag agt ggg tac cgg     2641
Met Met Val Asp Ser Thr Phe Tyr Asn Lys Ile Lys Ser Gly Tyr Arg
865                 870                 875                 880 atg gcc aag cct gac cac gct acc agt gaa gtc tac gag atc atg gtg     2689
Met Ala Lys Pro Asp His Ala Thr Ser Glu Val Tyr Glu Ile Met Val
            885                 890                 895 aaa tgc tgg aac agt gag ccg gag aag aga ccc tcc ttt tac cac ctg     2737
Lys Cys Trp Asn Ser Glu Pro Glu Lys Arg Pro Ser Phe Tyr His Leu
        900                 905                 910 agt gag att gtg gag aat ctg ctg cct gga caa tat aaa aag agt tat     2785
Ser Glu Ile Val Glu Asn Leu Leu Pro Gly Gln Tyr Lys Lys Ser Tyr
    915                 920                 925 gaa aaa att cac ctg gac ttc ctg aag agt gac cat cct gct gtg gca     2833
Glu Lys Ile His Leu Asp Phe Leu Lys Ser Asp His Pro Ala Val Ala
930                 935                 940 cgc atg cgt gtg gac tca gac aat gca tac att ggt gtc acc tac aaa     2881
Arg Met Arg Val Asp Ser Asp Asn Ala Tyr Ile Gly Val Thr Tyr Lys
            950                 955                 960
945
```

Fig. 2K

```
aac gag gaa gac aag ctg aag gac tgg gag ggt ctg gat gag cag       2929
Asn Glu Glu Asp Lys Leu Lys Asp Trp Glu Gly Leu Asp Glu Gln
        965                 970                 975 aga ctg agc gct gac agt ggc tac atc att cct ctg cct gac att gac   2977
Arg Leu Ser Ala Asp Ser Gly Tyr Ile Ile Pro Leu Pro Asp Ile Asp
        980                 985                 990 cct gtc cct gag gag gac gag ggc aag agg aac aga cac agc tcg       3025
Pro Val Pro Glu Glu Asp Glu Gly Lys Arg Asn Arg His Ser Ser
        995                 1000                1005 cag acc tct gaa gag agt gcc att gag acg ggt tcc agc agt tcc acc   3073
Gln Thr Ser Glu Glu Ser Ala Ile Glu Thr Gly Ser Ser Ser Thr
        1010                1015                1020 ttc atc aag aga gag gac gag acc att gaa gac atc gac atg atg gac   3121
Phe Ile Lys Arg Glu Asp Glu Thr Ile Glu Asp Ile Asp Met Met Asp
        1025                1030                1035            1040 gac atc ggc ata gac tct tca gac ctg gtg gaa gac agc ttc ctg taa   3169
Asp Ile Gly Ile Asp Ser Ser Asp Leu Val Glu Asp Ser Phe Leu
        1045                1050                1055 ctg gcg gat tcg agg gtt cct tcc act tct                           3199
Leu Ala Asp Ser Arg Val Pro Ser Thr Ser
        1060                1065
```

HUMAN PLATELET-DERIVED GROWTH FACTOR RECEPTOR

This is a Division of application Ser. No. 08/240,294 filed May 9, 1994, now U.S. Pat. No. 6,110,737, which is a file wrapper continuation of application Ser. No. 08/031,082, filed Mar. 15, 1993, now abandoned, which is a file wrapper continuation of application Ser. No. 07/771,829, filed Oct. 7, 1991, now abandoned, which is a file wrapper continuation of application Ser. No. 07/309,322, filed Feb. 10, 1989, now abandoned, which is a CIP of application Ser. No. 07/151,414, filed Feb. 2, 1988, now abandoned.

This invention was made with Government support under Grant No. RO 1 HL 32898 awarded by the National Institutes of Health. The Government has certain rights in this invention.

TECHNICAL FIELD

The present invention relates to growth factors and their receptors and, in particular, to human platelet-derived growth factor receptor.

BACKGROUND OF THE INVENTION

Platelet-derived growth factor (PDGF) is a major mitogen for cells of mesenchymal origin. The protein is a 32 kDa protein heterodimer composed of two polypeptide chains, A and B, linked by disulfide bonds. In addition to the PDGF AB heterodimer, two homodimeric forms of PDGF, denoted AA and BB, have been identified.

Until recently, whether the AA isoform bound to a receptor was not known. Now, a single receptor has been identified which has been shown to bind all three isoforms of hPDGF. However, the reported affinities of hPDGF receptors of different cell types for different isoforms of hPDGF has lead to speculation that there are more than one type of hPDGF receptor.

The first event in PDGF-mediated mitogenesis is the binding of PDGF to its receptor at the cell membrane. This interaction triggers a diverse group of early cellular responses including activation of receptor tyrosine kinase, increased phosphatidylinositol turnover, enhanced expression of a group of genes, activation of phospholipase A2, changes in cell shape, increase in cellular calcium concentration, changes in intracellular pH, and internalization and degradation of bound PDGF. These changes are followed by an increase in the rate of proliferation of the target cells.

While the ability of a polypeptide to stimulate growth of a particular cell type in vitro does not prove that it serves the same function in vivo, the role of many growth factors on cells is being studied to attempt to determine the role that the factors play in the whole organism. In vitro, platelet-derived growth factor is a major polypeptide mitogen in serum for cells of mesenchymal origin such as fibroblasts, smooth muscle cells and glial cells. In vivo, PDGF circulates stored in the a granules of blood platelets and does not circulate freely in blood. During blood clotting and platelet adhesion, the granules are released, often at sites of injured blood vessels, implicating PDGF in the repair of blood vessels. PDGF also stimulates migration of arterial smooth muscle cells from the medial to the intimal layer of the artery where they then proliferate as an early response to injury.

PDGF is being studied to determine how cell proliferation is controlled in the body. The growth factor has been implicated in wound healing, in atherosclerosis, and in stimulating genes associated with cancerous transformation of cells, particularly c-myc and c-fos. Therefore, PDGF agonists may be useful in promoting wound healing. PDGF antagonists may be useful in preventing atherosclerosis, in retarding blood vessel narrowing that occurs after cardiovascular intervention and in controlling cancerous proliferation.

Relevant Literature

The mouse PDGF receptor has been identified, purified (Daniel et al., *Proc. Natl. Acad. Sci USA* (1985) 82:2684–2687), and sequenced (Yarden et al., *Nature* (1986) 323:226–232). A cDNA sequence encoding a human PDGF receptor was identified, sequenced and used to transfect cells lacking the receptor (Escobedo et al., *Science* (1988) 240:1532–1538; Claesson-Welsh et al., *Mol. Cell. Biol.* (1988) 8:3476–3486). Studies using the transfected cells gave differing results, demonstrating that the receptor binds specifically to all three isoforms of hPDGF, preferentially binding the BB homodimer (Escobedo et al., supra.) and that the receptor binds the BB and AB isoforms but not the AA isoform, at least at the concentration tested (Claesson-welsh et al., supra.). Binding sites on different cell types were reported to have different affinities for different PDGF isoforms (Kazlauskas et al., *EMBO J.* (1988) 7:3727–3735). Two classes of PDGF receptor were reported to recognize different isoforms of PDGF (Hart et al., *Science* (1988) 240:1529–1531).

SUMMARY OF THE INVENTION

A DNA sequence encoding human platelet-derived growth factor receptor (hPDGF-R) has now been isolated and sequenced. An expression construct comprising the sequence encodes a receptor that can be secreted or incorporated into the membrane of a mammalian cell. The incorporated receptor is functionally equivalent to the wild-type receptor, conferring a PDGF-sensitive mitogenic response on cells lacking the receptor. The construct can be used for enhancing PDGF response of cells, determining the regions involved in transducing the signal in response to PDGF binding, providing mutated analogs and evaluating drugs for their physiologic activity.

BRIEF DESCRIPTION OF THE FIGURES

FIG. 1 shows the nucleotide sequence of a cDNA encoding B-hPDGF-R together with the deduced amino acid sequence of the receptor precursor.

FIGS. 2A–2E shows the nucleotide sequence of a cDNA encoding A-hPDGF-R together with the deduced amino acid sequence of the receptor.

DESCRIPTION OF SPECIFIC EMBODIMENTS

Methods for producing human platelet-derived growth factor (hPDGF-R) and nucleic and constructs for such production are provided as well as cells comprising the hPDGF-R where the composition and cells may find use in diagnosis, evaluation of drugs affecting the transduction of the hPDGF-R signal and in the treatment of diseases associated with hPDGF-R. The construct can be used to transfect cells, providing a membrane-bound receptor that is functionally equivalent to the wild-type receptor, and conferring a PDGF-sensitive mitogenic response on cells lacking the receptor. The transfected cells can be used as a model for studying the PDGF-induced response of cells, determining the regions involved in transducing the signal in response to PDGF binding and evaluating drugs for their physiologic activity. The encoded receptor or its binding region also find use in evaluating PDGF agonists. Other utilities for the DNA sequence include use of fragments of the sequence as probes to detect deletions in the region of chromosome 5 where a number of growth-control related genes are clustered, to detect deletions in chromosome 4 near the c-kit oncogene or to detect other genes encoding tyrosine kinase or homologous proteins.

The hPDGF receptor that binds the BB homodimer with high affinity has been variously referred as the B receptor, the β receptor and, as used herein, the type B receptor (B-hPDGF-R). The hPDGF receptor that preferentially binds the AA homodimer is referred to as the A receptor, the a receptor and, as used herein, the type A receptor (A-hPDGF-R).

The nucleotide sequence of a cDNA sequence encoding B-hPDGF-R is set forth in FIG. 1A–1D together with the deduced amino acid sequence of the receptor precursor. The sequence beginning at the amino acid. numbered 1 corresponds to the amino terminus of human PDGF-R. The first 32 amino acids (designated −32 to −1) encode the signal peptide sequence. The dark bar underlines the transmembrane sequence (amino acid residues 500 to 524). Potential N-glycosylation sites are indicated by a line. The polyadenylation site in the 3' end of the cDNA has been underlined.

TABLE 1

```
CGCTGGCTGCTGCAGCAGAGTGACTGCCGCCCTATCTGGGACCCAGGATCGCTCTGGAGCCAGAACTTGGAGCCAGAAGGAGGAGATCAACAAGGAGGAGAGAGCCGGCCCCTCAGCC
CTGCTGCCCAGCAGCAGCCTCTGCTCGCCCCTCCTCCATCCCTGTTCCTCCTGAGCCCTGCCAGGCCCCCTCGAGAGCGGAGCCTGCCACCAGTCCTGCCTCCTCGAGAAGATGTTGGGGAGTGAGGCGACATGGGGCCG
CTCCTCTCCCTACAGCACCCCTCCTCCCTGTTCCTCCTGAGCCCTGCCAGGCCCTGCCAGTCCTGCCACCAGTCCTGCCTCCTCGAGAAGATGTTGGGGAGTGAGGCGACATGGGGCCG

TTTCTGATAACTGGGAGGGCAGTAAGGAGACTTCCTGGAGGGGTGACTGTCCAGAGCCTGGAACTGTGCCCACCAGAAGCCATCAGCAGGAAGGACACC
```

```
                                                             -32          -30
                                                             Met  Arg  Leu
                                                             ATG  CGG  CTT
                                                                                                    1
Pro Gly Ala Met Pro Ala Leu Leu Ala Glu Leu Leu Leu Leu Ser Leu Leu Leu Glu Pro Gln Ile Ser Gln Gly Leu
CCG GGT GCG ATG CCA GCT CTG CTG GCC CTC GAG CTG CTC TTA CTT CTG TCT CTC TTG GAA CCA CAG ATC TCT CAG GGC CTG
                      -20                                -10
Val Val Thr Pro Pro Gly Pro Glu Leu Val Leu Asn Val Ser Ser Thr Phe Val Leu Thr Cys Ser Gly Ser Ala Pro Val Val Trp Glu
GTC GTC ACA CCC CCG GGG CCA GAG CTT GTC AAT GTC TCC AGC ACC TTC GTT CTG ACC TGC TCG GGT TCA GCT CCG GTG GTG TGG GAA
                                    20                                       30                                    60
Arg Met Ser Gln Pro Pro Gln Glu Met Ala Lys Ala Gln Asp Gly Thr Phe Ser Ser Val Leu Thr Leu Thr Asn Leu Thr Gly Leu
CGG ATG TCC CAG CCC CCA CAG GAG ATG GCC AAG GCC CAG GAT GGC ACC TTC AGC AGC GTG CTC ACC CTG ACC AAC CTC ACT GGG CTA
      40                                        50                                        60
Asp Thr Gly Glu Tyr Ile Cys Lys Lys Leu His Glu His His Val Thr Gln Gly Arg Lys Val Ala Gln Arg Val Leu Thr Val Arg Asp Ser Val Asn Ala Val Gln Thr Val Arg Gln Thr Val Val Asp Ser Gly Arg Leu Val Glu Ser Ala Glu Leu Glu Leu Ser Ala Glu Leu Glu Leu Leu Glu Pro Val Ala Leu Pro Val Ala Leu Pro Val Ala Leu Pro Val Ala Leu Pro Val Leu
```

*(Note: The sequence table shows nucleotide and amino acid sequences with numbered positions including -32, -30, -20, -10, 1, 20, 30, 40, 50, 60, 70, 80, 90, 100, 110, 120, 130, 140, 150, 160, 170, 180, 190, 200, 210, 220, 230, 240, 250, 260, 270, 280, 290, 300. Cys residues are boxed at positions 20, 70, 120, 170, 200, 260.)*

TABLE 1-continued

```
Lys Ala Ile Asn Ile Thr Val Val Glu Ser Gly Tyr Val Arg Leu Leu Gly Val Gly Thr Leu Gln Phe Ala Glu Leu His Arg Ser
AAG GCC ATC AAC ATC ACC GTG GTT GAG AGC GGC TAC GTG CGG GGA GAG GTG CTC CTG GGA ACA CAA TTT GCT GAG CTG CAT CGG AGC
                            310                             320                             330
Arg Thr Leu Gln Val Val Phe Glu Ala Tyr Pro Pro Thr Val Leu Trp Phe Lys Asp Arg Asn Arg Leu Gly Asp Ser Ser Ala Gly
CGG ACA CTG CAG TGA GTT TTC GAG GCC TAC CCG ACT GTC CTG TGG TTC AAA GAC CGC ACC CTG AGG GAC TCC AGC GCT GGC
                            340                             350                             360
Glu Ile Ala Leu Ser Thr Arg Asn Val Ser Glu Thr Leu Tyr Val Ser Glu Leu Thr Leu Ile Arg Val Lys Val Ala Glu Arg His
GAA ATC GCC CTG TCC ACG CGC AAC GTG TCG GAG ACC CTG TAT GTG TCA GAG CTG ACA CTG ATC CGC GTT AAG GTG GCA GAG GCT CAC
                            370                             380                             390
Tyr Thr Met Arg Ala Phe His Glu Asp Ala Asp Val Gln Leu Ser Phe Gln Leu Gln Ile Asn Val Pro Val Arg Val Leu Glu Leu Ser
TAC ACC ATG CGG GCC TTC CAT GAG GAT GCT GAT GTC CAG TTC CAG CTA CAG ATC AAT GTC CCT GTC CGA GTG CTG GAG CTA AGT
                            400                             410                             420
Glu Ser His Pro Asp Ser Gly Glu Gln Thr Val Arg Cys Arg Gly Arg Gly Met Pro Gln Asn Ile Ile Trp Ser Ala Cys Arg Asp
GAG AGC CAC CCT GAC AGT GGG GAA CAG ACA GTC CGC TGT CGT GGC CGG GGC ATG CCC CAG AAC ATC ATC TGG TCT GCC TGC AGA GAC
                            430                             440                             450
Leu Lyn Arg Cys Pro Arg Glu Leu Pro Pro Thr Leu Gly Asn Ser Ber Glu Glu Ser Gln Leu Glu Thr Cys Thr Leu Arg Tyr Trp
GTG AAA AGG TGT CCA CGT GAG CTG CCC ACG CTG CTG GGG AAC AGT TCC GAA GAG AGC CAG CTG GAG ACT TGC ACG CTG AGA TAC TGG
                            460                             470                             480
Glu Glu Glu Phe Glu Val Val Ser Val Asp Arg Leu Gln His Val Asp His Asp Pro Lys Ser Val Val Ile Ser Ala Leu Val Val
GAG GAG GAG TTT GAG GTG GTG AGC GTG GAC CGT CTG CAG CAC GTG GAT CAT GAT CCC AAG TCG GTG GTC ATC TCA GCC CTG GTG GTG
                            490                             500                             510
Val Gly Gln Thr Asp Gln Glu Val Ile Val Pro His Ser Leu Pro Phe Lys Pro Arg Tyr Glu Ile Arg Trp Lys Val Ile Glu Ser Val Ser
GTG GGC CAG ACG GAC CAG GAG GTC ATC GTG CCA CAC TCC CTT CCC TTT AAG CCA CGT TAC GAG ATC CGA TGG AAG GTG ATT GAG TCT GTG AGC
                            520                             530                             540
Leu Thr Ile Ile Ser Leu Ile Ile Met Leu Ile Met Leu Trp Gln Lys Lys Pro Arg Tyr Glu Ile Arg Trp Lys Val Ile Glu Ser Val Ser
CTC ACC ATC ATC TCC CTT ATC ATC ATG CTC ATG CTT TGG CAG AAG AAG CCA
                            550                             560                             570
Ser Asp Gly His Glu Tyr Ile Tyr Val Asp Pro Met Gln Leu Pro Tyr Asp Ser Thr Trp Glu Leu Pro Arg Asp Gln Leu Val Leu Gly
TCT GAC CAT GAG TAC ATC TAC GTG GAC CCC ATG CAG CTG CCC TAT GAC TCC ACG TGG GAG CTG CCG CGG GAC CAG CTT GTG CTG GGA
                                                             580                             590                             600
Arg Thr Leu Gly Ser Gly Ala Phe Gly Gln Val Val Glu Ala Thr Ala His Gly Leu Ser His Ser Gln Ala Thr Met Lys Val Ala Val
CGC ACC CTC GGC TCT GGG GCC TTT GGC CAG GTG GTG GAG GCC ACG GCT CAT GGC CTG AGC CAT TCT CAG GCC ACG ATG AAA GTG GCC GTC
                                                             610                             620                             630
Lys Met Leu Lys Ser Thr Ala Arg Ser Ser Glu Lys Gln Ala Leu Met Ser Glu Leu Lys Ile Met Ser His Leu Gly Pro His Leu Asn
AAG ATG CTT AAA TCC ACA GCC CGC AGC AGT GAG AAG CAA GCC CTT ATG TCG GAG CTG AAG ATC ATG AGT CAC CTG GGG CCC CAC CTG AAC
```

TABLE 1-continued

```
                        640                                             650                                             660
Val Val Asn Leu Gly Ala Cys Lys Gly Gly Pro Ile Ile Tyr Thr Glu Tyr Cys Arg Tyr Gly Asp Leu Val Asp Tyr Leu
GTG GTC AAC CTG GGG GCC TGC AAA GGA GGA CCC ATC ATC ACT GAG TAC TGC CGC TAC GGA GAC CTG GTG GAC TAC CTG
                        670                                             680                                             690
His Arg Asn Lys His Thr Phe Leu Gln His His Ser Asp His Ser Asp Lys Arg Pro Pro Ser Ala Glu Leu Tyr Ser Asn Ala Leu Pro Val Gly
CAC CGC AAC AAA CAC ACC TTC CTG CAG CAC CAC TCC GAC CAC AGC GAC AAG CGC CCG CCG AGC GAG CTG TAC AGC GCC CTG CCC GTT GGG
                        700                                             710                                             720
Val Pro Ser His Val Ser Leu Thr Gly Glu Ser Asp Gly Gly Tyr Met Asp Met Ser Lys Asp Glu Ser Val Asp Tyr Val Pro
CTC CCC AGC CAT GTG TCC CTC ACC GGT GAG AGC GAC GGG GGT TAC ATG GAC ATG AGC AAG GAC GAG TCG GTG GAC TAT GTG CCC
                        730                                             740                                             750
Met Leu Asp Met Lys Gly Asp Val Lys Tyr Ala Asp Ile Glu Ser Ser Asn Tyr Met Ala Pro Tyr Asp Asn Tyr Val Pro Ser Ala Pro
ATG CTG GAC ATG AAA GGA GAC GTC AAA TCT GCA GAC ATC GAG TCC TCC AAC TAC ATG GCG CCT TAC GAT AAC TAC GTT CCT TCC GCC CCT
                        760                                             770                                             780
Glu Arg Thr Cys Arg Ala Thr Leu Ile Asn Glu Ser Pro Val Leu Ser Tyr Met Asp Leu Val Gly Phe Ser Tyr Gln Val Ala Asn Gly
GAG AGG ACC TGC CGA GCA ACT TTG ATC AAC GAG TCT CCA GTG CTA AGC TAC ATG GAC CTC GTG GGC TTC AGC TAC CAG GTG GCC AAT GGC
                        790                                             800                                             810
Met Glu Phe Leu Ala Ser Lys Asn Cys Val His Arg Asp Leu Ala Ala Arg Asn Val Leu Ile Cys Glu Gly Lys Leu Val Ile Cys
ATG GAG TTT CTG GCC TCC AAG AAC TGC GTC CAC AGA GAC CTG GCG GCT AGG AAC GTG CTC ATC TGT GAA GGC AAG CTG GTC ATC TGT
                        820                                             830                                             840
Asp Phe Gly Leu Ala Arg Asp Ile Met Arg Asp Ser Asn Tyr Ile Ser Lys Gly Ser Thr Phe Leu Pro Leu Lys Trp Met Ala Pro Glu
GAC TTT GGG CTG GCT CGA GAT ATC ATG CGG GAC AGC AAT TAC ATC TCC AAA GGC AGC ACC TTT TTG CCT TTA AAG TGG ATG GCT CCG GAG
                        850                                             860                                             870
Ser Ile Phe Asn Ser Leu Tyr Thr Thr Leu Ser Asp Val Trp Ser Phe Gly Ile Leu Leu Trp Glu Ile Phe Thr Leu Gly Gly Thr Pro
AGC ATC TTC AAC AGC CTC TAC ACC ACC CTG AGC GAC GTG TGG TCC TTC GGG ATC CTG CTG TGG GAG ATC TTC ACC TTG GGT GGA ACC CCT
                        880                                             890                                             900
Tyr Pro Glu Leu Pro Met Asn Glu Gln Phe Tyr Asn Ala Ile Lys Arg Gly Tyr Arg Met Ala Gln Pro Ala His Ala Ser Asp Glu Ile
TAC CCA GAG CTG CCC ATG AAT GAG CAG TTC TAC AAT GCC ATC AAA AGA GGT TAC CGC ATG GCC CAG CCT GCC CAT GCC TCC GAC GAG ATC
                        910                                             920                                             930
Tyr Glu Ile Met Gln Lys Cys Trp Glu Lys Phe Glu Ile Arg Pro Pro Phe Ser Gln Leu Val Leu Leu Leu Glu Arg Leu Leu Gly
TAT GAG ATC ATG CAG AAG TGC TGG GAA AAG TTT GAG ATT CGG CCC CCC TTC TCC CAG CTG GTG CTG CTT CTC GAG AGA CTG TTG GGC
                        940                                             950                                             960
Glu Gly Tyr Lys Lys Tyr Gln Gln Val Asp Glu Glu Phe Leu Arg Ser Asp His Pro Ala Ile Leu Arg Ser Gln Ala Arg Leu Pro
GAA GGT TAC AAA AAG TAC CAG CAG GTG GAT GAG GAG TTT CTG AGG AGT GAC CAC CCA GCC ATC CTT CGG TCC CAG GCC CGC TTG CCT
                        970                                             980                                             990
Gly Phe His Gly Leu Arg Ser Pro Leu Asp Thr Ser Ser Val Leu Tyr Thr Ala Val Gln Pro Asn Glu Gly Asp Asn Asp Tyr Ile Ile
GGG TTC CAT GGC CTC CGA TCT CCC CTG GAC ACC AGC AGT GTC CTC TAT ACT GCC CAG CCC AAT GAG GGT GAC AAC GAC TAT ATC ATC
                        1000                                            1010                                            1020
Pro Leu Pro Asp Pro Lys Pro Glu Val Ala Asp Glu Gly Pro Leu Glu Gly Ser Pro Ser Leu Ala Ser Ser Thr Leu Asn Glu Val Asn
```

TABLE 1-continued

```
CCC CTG CCT GAC CCC AAA CCC GAG GTT GCT GAC GAG GGC CCA CTG GAG GGT TCC CCC AGC TCC ACC CTG AAT GAA GTC AAC
                                                                                                1050
Thr Ser Ser Thr Ile Ser Cys Asp Ser Pro Leu Glu Pro Gln Asp Glu Pro Gln Leu Glu Leu Gln Val Glu Pro Glu
            1030
ACC TCC TCA ACC ATC TCC TGT GAC AGC CCC CTG GAG CCC CTA GAG CCA GAG CCC CAG CCC CTT CAG GTG GAG GAG CCG GAG

Pro Glu Leu Gln Leu Pro Asp Ser Gly Cys Pro Ala Pro Arg Ala Glu Ala Glu Asp Ser Phe Leu AH
                        1060                                                            1074
CCA GAG CTG CAG CTG CCA GAT TCG GGG TGC CCT GCG CCT CGG GAA GCA GAG GAT AGC TTC CTG TAG GGGGCTGGCCCCTACCCTGCCCTG

CCTGAAGCTCCCCGCTGCCAGACCCAGCAGCATCCTGCCTGGCCTTCTGTCAGCCAGGCTCGCCCTTATCAGCTGTCCCTTCTGGAAGCTTTCTGCTCCTGACGTGTT
GTGCCCCAAACCCTGGGGCTGGCTTAGGAGGACAAGAAAACTGACCAGCCCTCTGCCTCCAGGGAGGCCAACTGACTCTGAGCCAGGGTTCCCCAGGGAACTCAGTTTT
CCCATATGTAAAATGGAAAGTTAGGCTTCAGCCAGCTACCCCTCAAGGAATCATAGCTCTCTCCTGCACTTATCACCCAGAGACCTAGGGAAGATTCTTGAGTGAGTGGTA
AATTAACTTTTTTCTGTTCAGCCAGCTACCCCTCAAGGAATCATAGCTCTCTCCTCCTATGATGGCCAGTAAATGCGTTCCCTGGGCCATTAGCAGCCATTAATGCTGG
AGGCTGAGCCAAGTACAGGACGACTCTGCCTCATCCAGAAGAACCAGTCTCCTCCCAGCACTTGAGCACCATAGCAAGTCTGTCCTTCCTTCAGGCCCATCAGTCCTCAGTGGCTTTTT
CTTTATCACCCTCCAGTCTTTAATCATCCACAGAGTCTTAGAAGGCCAGAGCCCGCCAGTCTGATGAATGTAAATGTGGAGTGGCCACGTGTGTTGCCAGTATATG
GCCCTGGCTCTGCATGGACCTGCTATGAGGGCTTTGCACATTTGCACATTGTCCAGGCCCCAGAAGCAAGCCATATACCTAAACTTCATCTGGGGGTCAGCTAGAGTGACTCCTGGGAGATTCAGATCACACATC
ACACTCTGGGACTTCAGAAGAACCATGCCCCCTTCCCAGGCCCCAGAAGCAAGCCATATACCTAAACTTCATCTGGGGGTCAGCTAGAGTGACTCCTGGGAGATTCAGATCACACAGCTG
CCCAGGACATGGAAGACCTCTTTCACTACCCAGATGACCTCCGGGGTATCCTGGGCAAAAGGGCAAATGACAAATGAGAGGCCAAATGAGATCACCTCCTGCAGCCCACCACTCCAG
CACCTGTGCCGAGTCTGCGTCGAAGACAGAATGGACAGTTATGTCTTGAAAAGACAACAGAAGCCTCAGAGTGGTACCCCAAGAAGATGTGAGAGTTGAGAGGTTGGGCGCTTTGA
GGTTTGCCCCTCCACCCAGCTGCCCATCCTGAGGCAGCCCGACGGGGAAGGGTTGTCACTGCCCAGAGCTGACAGTGACATCTCATTGTCCCAGCCAGTGGCACGCATTGGA
GGGATCCCAGAGTTGGTCCAAGAGGAGTGGGTTCTCAATACGTACCAAAGATATAATCACCTAGGTTTACAAATATTTTAGGACTCACGTTAACTCACATTTATACAGCAGAA
ATGCTATTTTTGTGATGCTGTTAAGTTTTTTCTATCTGTTACTTTTTTTTAAGGAAAGATTTTAATATTTAAACCTGGTCTCTTCTCAAAAAAAAAAAAAAAAAAAAA
```

The nucleotide sequence of a cDNA sequence encoding A-hPDGF-R is set forth in FIGS. 2A–2E together with the deduced amino acid sequence of the receptor. The sequence of the 3' untranslated region and the signal sequence-encoding region are not shown. The reading frame for the amino acid sequence begins at nucleotide 2. The "*" at nucleotides 3167–3169 (TAA) indicates a stop codon for chain termination of the receptor protein sequence. The coding sequence for the extracellular domain is from nucleotide 1 through 1471. The transmembrane region is from 1472 through 1546. The intracellular region is from 1547–3166. The tyrosine kinase region is encoded by residues 1669–1982 and 2279 to about 2700.

TABLE 2

| | | | | | | | | | | | | | |
|---|---|---|---|---|---|---|---|---|---|---|---|---|---|
| 1 | AAA | TGA | AAA | GGT | TGT | GCA | GCT | GAA | TTC | ATC | CTT | TTC | TCT | GAG | 42 |
| | Asn | Glu | Lys | Val | Val | Gln | Leu | Asn | Ser | Ser | Phe | Ser | Leu | Arg | |
| 43 | ATG | CTT | TGG | GGA | GAG | TGA | AGT | GAG | CTG | GCA | GTA | CCC | CAT | GTC | 84 |
| | Cys | Phe | Gly | Glu | Ser | Glu | Val | Ser | Trp | Gln | Tyr | Pro | Met | Ser | |
| 85 | TGA | AGA | AGA | GAG | CTC | CGA | TGT | GGA | AAT | CAG | AAA | TGA | AGA | AAA | 126 |
| | Glu | Glu | Glu | Ser | Ser | Asp | Val | Glu | Ile | Arg | Asn | Glu | Glu | Asn | |
| 127 | CAA | CAG | CGG | CCT | TTC | TGT | GAC | GGT | CTT | GGA | AGT | GAG | CAG | TGC | 168 |
| | Asn | Ser | Gly | Leu | Ser | Val | Thr | Val | Leu | Glu | Val | Ser | Ser | Ala | |
| 169 | CTC | GGC | GGC | CCA | CAC | AGG | GTT | GTA | CAC | TTG | CTA | TTA | CAA | CCA | 210 |
| | Ser | Ala | Ala | His | Thr | Gly | Leu | Tyr | Thr | Cys | Tyr | Tyr | Asn | His | |
| 211 | CAC | TCA | GAC | AGA | AGA | GAA | TGA | GCT | TGA | AGG | CAG | GCA | CAT | TTA | 252 |
| | Thr | Gln | Thr | Glu | Glu | Asn | Glu | Leu | Glu | Gly | Arg | His | Ile | Tyr | |
| 253 | CAT | CTA | TGT | GCC | AGA | CCC | AGA | TGT | AGC | CTT | TGT | ACC | TCT | AGG | 294 |
| | Ile | Tyr | Val | Pro | Asp | Pro | Asp | Val | Ala | Phe | Val | Pro | Leu | Gly | |
| 295 | AAT | GAC | GGA | TTA | TTT | AGT | CAT | CGT | GGA | GGA | TGA | TGA | TTC | TGC | 336 |
| | Met | Thr | Asp | Tyr | Leu | Val | Ile | Val | Glu | Asp | Asp | Asp | Ser | ALa | |
| 337 | CAT | TAT | ACC | TTG | TCG | CAC | AAC | TGA | TCC | CGA | GAC | TCC | TGT | AAC | 372 |
| | Ile | Ile | Pro | Cys | Arg | Thr | Thr | Asp | Pro | Glu | Thr | Pro | Val | Thr | |
| 379 | CTT | ACA | CAA | CAG | TGA | GGG | GGT | GGT | ACC | TGC | CTC | CTA | CGA | CAG | 420 |
| | Leu | His | Asn | Ser | Glu | Gly | Val | Val | Pro | Ala | Ser | Tyr | Asp | Ser | |
| 421 | CAG | ACA | GGG | CTT | TAA | TGG | GAC | CTT | CAC | TGT | AGG | GCC | CTA | TAT | 462 |
| | Arg | Gln | Gly | Phe | Asn | Gly | Thr | Phe | Thr | Val | Gly | Pro | Tyr | Ile | |
| 463 | CTG | TGA | GGC | CAC | CGT | CAA | AGG | AAA | GAA | GTT | CCA | GAC | CAT | CCC | 504 |
| | Cys | Glu | Ala | Thr | Val | Lys | Gly | Lys | Lys | Phe | Gln | Thr | Ile | Pro | |
| 505 | ATT | TAA | TGT | TTA | TGC | TTT | AAA | AGC | AAC | ATC | AGA | GCT | GGA | TCT | 546 |
| | Phe | Asn | Val | Tyr | Ala | Leu | Lys | Ala | Thr | Ser | Glu | Leu | Asp | Leu | |
| 547 | AGA | AAT | GGA | AGC | TCT | TAA | AAC | CGT | GTA | TAA | GTC | AGG | GGA | AAC | 589 |
| | Glu | Met | Glu | Ala | Leu | Lys | Thr | Val | Tyr | Lys | Ser | Gly | Glu | Thr | |
| 589 | GAT | TGT | GGT | CAC | CTG | TGC | TGT | TTT | TAA | CAA | TGA | GGT | GGT | TGA | 630 |
| | Ile | Val | Val | Thr | Cys | Ala | Val | Phe | Asn | Asn | Glu | Val | Val | Asp | |
| 631 | CCT | TCA | ATG | GAC | TTA | CCC | TGG | AGA | AGT | GAA | AGG | CAA | AGG | CAT | 672 |
| | Leu | Gln | Trp | Thr | Tyr | Pro | Gly | Glu | VAl | Lys | Gly | Lys | Gly | Ile | |
| 673 | CAC | AAT | GCT | GGA | AGA | AAT | CAA | AGT | CCC | ATC | CAT | CAA | ATT | GGT | 714 |
| | Thr | Met | Leu | Glu | Glu | Ile | Lys | Val | Pro | Ser | Ile | Lys | Leu | Val | |
| 715 | GTA | CAC | TTT | GAC | GGT | CCC | CGA | GGC | CAC | GGT | GAA | AGA | CAG | TGG | 756 |
| | Tyr | Thr | Leu | Thr | Val | Pro | Glu | Ala | Thr | Val | Lys | Asp | Ser | Gly | |
| 757 | AGA | TTA | CGA | ATG | TGC | TGC | CCG | CCA | GGC | TAC | CAG | GGA | GGT | CAA | 798 |
| | Asp | Tyr | Glu | Cys | Ala | Ala | Arg | Gln | Ala | Thr | Arg | Glu | Val | Lys | |
| 799 | AGA | AAT | GAA | GAA | AGT | CAC | TAT | TTC | TGT | CAA | TGA | AAA | AGG | TTT | 840 |
| | Glu | Met | Lys | Lys | Val | Thr | Ile | Ser | Val | His | Glu | Lys | Gly | Phe | |
| 841 | CAT | TGA | AAT | CAA | ACC | CAC | CTT | CAG | CCA | GTT | GGA | AGC | TGT | CAA | 882 |
| | Ile | Glu | Ile | Lys | Pro | Thr | Phe | Ser | Gln | Leu | Glu | Ala | Val | Asn | |
| 883 | CCT | GCA | TGA | AGT | CAA | ACA | TTT | TGT | TGT | AGA | GGT | GCG | GGC | CTA | 924 |
| | Leu | His | Glu | Val | Lys | His | Phe | Val | Val | Glu | Val | Arg | Ala | Tyr | |
| 925 | CCC | ACC | TCC | CAG | GAT | ATC | CTG | GCT | GAA | AAA | CAA | TCT | GAC | TCT | 966 |
| | Pro | Pro | Pro | Arg | Ile | Ser | Trp | Leu | Lys | Asn | Asn | Leu | Thr | Leu | |

TABLE 2-continued

```
 967 GAT TGA AAA TCT CAC TGA GAT CAC CAC TGA TGT GGA AAA GAT 1008
     Ile Glu Asn Leu Thr Glu Ile Thr Thr Asp Val Glu Lys Ile

1009 TCA GGA AAT AAG GTA TCG AAG CAA ATT AAA GCT GAT CCG TGC 1050
     Gln Glu Ile Arg Tyr Arg Ser Lys Leu Lys Leu Ile Arg Ala

1051 TAA CCA AGA AGA CAG TGG CCA TTA TAC TAT TGT AGC TCA AAA 1092
     Asn Gln Glu Asp Ser Gly His Tyr Thr Ile Val Ala Gln Asn

1093 TGA AGA TGC TGT GAA GAG CTA TAC TTT TGA ACT GTT AAC TCA 1134
     Glu Asp Ala Val Lys Ser Tyr Thr Phe Glu Leu Leu Thr Glu

1135 AGT TCC TTC ATC CAT TCT GGA CTT GGT CGA TGA TCA AGG TGG 1176
     Val Pro Ser Ser Ile Leu Asp Leu Val Asp Asp His His Gly

1177 CTC AAC TGG GGG ACA GAC GGT GAG GTG CAC AGC TGA AGG CAC 1218
     Ser Thr Gly Gly Gln Thr Val Arg Cys Thr Ala Glu Gly Thr

1219 GCC GCT TCC TGA TAT TGA GTG GAT GAT ATG CAA AGA TAT TAA 1260
     Pro Leu Pro Asp Ile Glu Trp Met Ile Cys Lys Asp Ile Lys

1261 GAA ATG TAA TAA TGA AAC TTC CTG GAC TAT TTT GGC CAA CAA 1302
     Lys Cys Asn Asn Glu Thr Ser Trp Thr Ile Leu Ala Asn Asn

1303 TGT CTC AAA CAT CAT CAC GGA GAT CCA CTC CCG AGA CAG GAG 1344
     Val Ser Asn Ile Ile Thr Glu Ile His Ser Arg Asp Arg Ser

1345 TAC CGT GGA GGG CCG TGT GAC TTT CGC CAA AGT GGA GGA GAC 1386
     Thr Val Glu Gly Arg Val Thr Phe Ala Lys Val Glu Glu Thr

1387 CAT CGC CGT GCG ATG CCT GGC TAA GAA TCT CCT TGG AGC TGA 1428
     Ile Ala Val Arg Cys Leu Ala Lys Asn Leu Leu Gly Ala Glu

1429 GAA CCG AGA GCT GAA GCT GGT GGC TCC CAC CCT GCG TTC TGA 1470
     Asn Arg Glu Leu Lys Leu Val Ala Pro Thr Leu Arg Ser Glu

1471 ACT CAC GGT GGC TGC TGC AGT CCT GGT GCT GTT GGT GAT TGT 1512
     Leu Thr Val Ala ALa Ala Val Leu Val Leu Leu Val Ile Val

1513 GAT CAT CTC ACT TAT TGT CCT GGT TGT CAT TTG GAA ACA GAA 1554
     Ile Ile Ser Leu Ile Val Leu Val Ile Trp Lys Gln Lys

1555 ACC GAG GTA TGA AAT TCG CTG GAG GGT CAT TGA ATC AAT CAG 1596
     Pro Arg Tyr Glu Ile Arg Trp Arg Val Ile Glu Ser Ile Ser

1597 CCC GGA TGG ACA TGA ATA TAT TTA TGT GGA CCC GAT GCA GCT 1638
     Pro Asp Gly His Glu Tyr Ile Tyr Val Asp Pro Met Gln Leu

1639 GCC TTA TGA CTC AAG ATG GGA GTT TCC AAG AGA TGG ACT AGT 1680
     Pro Tyr Asp Ser Arg Trp Glu Phe Pro Arg Asp Gly Leu Val

1681 GCT TGG TCG GGT CTT GGG GTC TGG AGC GTT TGG GAA GGT GGT 1722
     Leu Gly Arg Val Leu Gly Ser GLy Ala Phe Gly Lys Val Val

1723 TGA AGG AAC AGC TA TGG ATT AAG CCG TCC CAA CCT GTC AT 1764
     Glu Gly Thr Ala Tyr Gly Leu Ser Arg Ser Gln Pro Val Met

1765 GAA AGT TGC AGT GAA CAT GCT AAA ACC CAC GGC CAG ATC CAG 1806
     Lys Val Ala Val Asn Met Leu Lys Pro Thr Ala Arg Ser Ser

1807 TGA AAA ACA AGC TCT CAT GTC TGA ACT GAA GAT AAT GAC TCA 1848
     Glu Lys Gly Ala Leu Met Ser Glu Leu Lys Ile Met Thr His

1849 CCT GGG GCC ACA TTT GAA CAT TGT AAA CTT GCT GGG AGC CTG 1890
     Leu Gly Pro His Leu Asn Ile Val Asn Leu Leu Gly Ala Cys

1891 CAC CAA GTC AGG CCC CAT TTA CAT CAT CAC AGA GTA TTG CTT 1932
     Thr Lys Ser Gly Pro Ile Tyr Ile Ile Thr Glu Tyr Cys Phe

1933 CTA TGG AGA TTT GGT CAA CTA TTT GCA TAA GAA TAG GGA TAG 1974
     Tyr Gly Asp Leu Val Asn Tyr Leu His Lys Asn Arg Asp Ser

1975 CTT CCT GAG CCA CCA CCC AGA GAA GCC AAA GAA AGA GCT GGA 2016
     Phe Leu Ser His His Pro Glu Lys Pro Lys Lys Glu Leu Asp

2017 TAT CTT TGG ATT GAA CCC TGC TGA TGA AAG CAC ACG GAG CTA 2058
     Ile Phe Gly Leu Asn Pro Ala Asp Glu Ser Thr Arg Ser Tyr

2059 TGT TAT TTT ATC TTT TGA AAA CAA TGG TGA CTA CAT GGA CAT 2100
```

TABLE 2-continued

```
     Val Ile Leu Ser Phe Glu Asn Asn Gly Asp Tyr Met Asp Met
2101 GAA GCA GGC TGA TAC TAC ACA GTA TGT CCC CAT GCT AGA AAG 2142
     Lys Gln Ala Asp Thr Thr Gln Tyr Val Pro Met Leu Glu Arg

2143 GAA AGA GGT TTC TAA ATA TTC CGA CGT CCA GAG ATC ACT CTA 2184
     Lys Glu Val Ser Lys Tyr Ser Asp Val Gln Arg Ser Leu Tyr

2185 TGA TCG TCC AGC CTC ATA TAA GAA GAA ATC TAT GTT AGA CTC 2226
     Asp Arg Pro Ala Ser Tyr Lys Lys Lys Ser Met Leu Asp Ser

2227 AGA AGT CAA AAA CCT CCT TTC AGA TGA TAA CTC AGA AGG CCT 2268
     Glu Val Lys Asn Leu Leu Ser Asp Asp Asn Ser Glu Gly Leu

2269 TAC TTT ATT GGA TTT GTT GAG CTT CAC CTA TCA AGT TGC CCG 2310
     Thr Leu Leu Asp Leu Leu Ser Phe Thr Tyr Gln Val Ala Arg

2311 AGG AAT GGA GTT TTT GGC TTC AAA AAA TTG TGT CCA CCG TGA 2352
     Gly Met Glu Phe Leu Ala Ser Lys Asn Cys Val His Arg Asp

2353 TCT GGC TGC TCG CAA CGT CCT CCT GGC ACA AGG AAA AAT TGT 2394
     Leu Ala Ala Arg Asn Val Leu Leu Ala Gln Gly Lys Ile Val

2395 GAA GAT CTG TGA CTT TGG CCT GGC CAG AGA CAT CAT GCA TGA 2436
     Lys Ile Cys Asp Phe Gly Leu Ala Arg Asp Ile Met His Asp

2437 TTC GTT CTA TGT GTC GAA AGG CAG TAC CTT TCT GAC CGT GAA 2479
     Ser Phe Tyr Val Ser Lys Gly Ser Thr Phe Leu Pro Val Lys

2479 GTG GAT GGC TCC TGA GAG CAT CTT TGA CAA CCT CTA CAC CAC 2520
     Trp Met Ala Pro Glu Ser Ile Phe Asp Asn Leu Tyr Thr Thr

2521 ACT GAG TGA TGT CTG GTC TTA TGG CAT TCT GCT CTG GGA GAT 2562
     Leu Ser Asp Val Trp Ser Tyr Gly Ile Leu Leu Trp Glu Ile

2563 CTT TTC CCT TGG TGG CAC CCC TTA CCC CGG CAT GAT GGT GGA 2604
     Phe Ser Leu Gly Gly Thr Pro Tyr Pro Gly Met Met Val Asp

2605 TTC TAC TTT CTA CAA TAA GAT CAA GAG TGG GTA CCG GAT GGA 2646
     Ser Thr Phe Tyr Asn Lys Ile Lys Ser Gly Tyr Arg Met Ala

2647 CAA GCC TGA CCA CGC TAC CAG TGA AGT CTA CGA GAT CAT GGT 2689
     Lys Pro Asp His Ala Thr Ser Glu Val Tyr Glu Ile Met Val

2689 GAA ATG CTG GAA CAG TGA GCC GGA GAA GAG ACC CTC CTT TTA 2730
     Lys Cys Trp Asn Ser Glu Pro Glu Lys Arg Pro Ser Phe Tyr

2731 CCA CCT GAG TGA GAT TGT GGA GAA TCT GCT GCC TGG ACA ATA 2772
     His Leu Ser Glu Ile Val Glu Asn Leu Leu Pro Gly Gln Tyr

2773 TAA AAA GAG TTA TGA AAA AAT TCA CCT GGA CTT CCT GAA GAG 2814
     Lys Lys Ser Tyr Glu Lys Ile His Leu Asp Phe Leu Lys Ser

2815 TGA CCA TCC TGC TGT GGC ACG CAT GCG TGT GGA CTC AGA CAA 2856
     Asp His Pro Ala Val Ala Arg Met Arg Val Asp Ser Asp Asn

2857 TGC ATA CAT TGG TGT CAC CTA CAA AAA CGA GGA AGA CAA GCT 2898
     Ala Tyr Ile Gly Val Thr Tyr Lys Asn Glu Glu Asp Lys Leu

2899 GAA GGA CTG GGA GGG TGG TCT GGA TGA GCA GAG ACT GAG CGC 2940
     Lys Asp Trp Glu Gly Gly Leu Asp Glu Gln Arg Leu Ser Ala

2941 TGA CAG TGG CTA CAT CAT TCC TCT GCC TGA CAT TGA CCC TGT 2982
     Asp Ser Gly Tyr Ile Ile Pro Leu Pro Asp Ile Asp Pro Val

2983 CCC TGA GGA GGA GGA CCT GGG CAA GAG GAA CAG ACA CAG CTC 3024
     Pro Glu Glu Glu Asp Leu Gly Lys Arg Asn Arg His Ser Ser

3025 GCA GAC CTC TGA AGA GAG TGC CAT TGA GAC GGG TTC AGC AGC 3066
     Gln Thr Ser Glu Glu Ser Ala Ile Glu Thr Gly Ser Ser Ser

3067 TTC CAC CTT CAT CAA GAG AGA GGA CGA GAC CAT TGA AGA CAT 3108
     Ser Thr Phe Ile Lys Arg Glu Asp Glu Thr Ile Glu Asp Ile

3109 CGA CAT GAT GGA CGA CAT CGG CAT AGA CTC TTC AGA CCT GGT 3150
     Asp Met Met Asp Asp Ile Gly Ile Asp Ser Ser Asp Leu Val
```

TABLE 2-continued

```
3151 GGA AGA CAG CTT CCT GTA ACT GGC GGA TTC GAG GGT TCC TTC  3192
     Glu Asp Ser Phe Leu  *  Leu Ala Asp Ser Arg Val Pro Ser

3193 CAC TTC T                                                 3199
     Thr Ser
```

As seen in Tables 1 and 2, the intracellular, tyrosine kinase domain of the type A and type B receptors have about 80% identical residues. The extracellular domain of the type A and B receptors have about 34–35% identical residues, an additional 14% of the remaining residues being conservative substitutions. The transmembrane regions of the hPDGF receptors have about 48% identical residues. Of the 52% of residues that differ, 70% are conservative substitutions. As seen in the tables, both receptor sequences have a 107 amino acid insertion interrupting the tyrosine kinase region (encoded by residues 1983–2278 of type A).

The DNA compositions of this invention may be derived from genomic DNA or cDNA, prepared by synthesis or combinations thereof. The DNA compositions may include the complete coding region encoding hPDGF-R or fragments thereof of interest, usually comprising at least 8 codons (24 bp), more usually at least 12 codons, where one or more introns may be present. while for the most part the wild-type sequence will be employed, in some situations one or more mutations may be introduced, such as deletions, substitutions or insertions resulting in changes in the amino acid sequence or providing silent mutations. The genomic sequence will usually not exceed 50 kbp, more usually not exceed about 10 kbp, preferably not greater than 6 kbp.

A DNA fragment encoding hPDGF-R finds use to isolate DNA encoding PDGF receptors of other species which share substantial homologies with hPDGF-R. Fragments from the intracellular tyrosine kinase region can be used to isolate other tyrosine kinases. Portions of the DNA fragment having at least about 10 nucleotides, usually at least about 20 nucleotides, and fewer than about 6 knt (kilonucleotides), usually fewer than about 0.5 knt, from a DNA sequence encoding hPDGF-R find use as probes. The probes can be used to determine whether mRNA encoding hPDGF-R is present in a cell.

Additionally, the type B human PDGF receptor gene is located at a site on chromosome 5 where a number of growth control related genes are clustered. At least one genetic disease, 5q minus syndrome, has been shown to involve a deletion in this region. The type A receptor gene is located on chromosome 4 near the c-kit oncogene. Fragments of the hPDGF-R gene sequence may be used as a marker to probe the structure of these important regions of the genome and to diagnose genetic diseases associated with those areas of the genome.

The DNA fragment or portions thereof can also be used to prepare an expression construct for hPDGF-R. The construct comprises one or more DNA sequences encoding hPDGF-R under the transcriptional control of the native or other than the native promoter. When more than one sequence encoding hPDGF-R is present in the construct, the sequences may encode the same or different isoforms of the receptor, usually different. Usually the promoter will be a eukaryotic promoter for expression in a mammalian cell, where the mammalian cell may or may not lack PDGF receptors. In cases where one wishes to expand the DNA sequence or produce the receptor protein or fragments thereof in a prokaryotic host, the promoter may also be a prokaryotic promoter. Usually a strong promoter will be employed to provide for high level transcription and expression.

The expression construct may be part of a vector capable of stable extrachromosomal maintenance in an appropriate cellular host or may be integrated into host genomes. The expression cassette may be bordered by sequences which allow for insertion into a host, such as transposon sequences, lysogenic viral sequences, or the like. Normally, markers are provided with the expression cassette which allow for selection of host cells containing the expression cassette. The marker may be on the same or a different DNA molecule, desirably the same DNA molecule.

In mammalian cells, the receptor gene itself may provide a convenient marker. However, in prokaryotic cells, markers such as resistance to a cytotoxic agent, complementation of an auxotrophic host to prototrophy, production of a detectable product, etc. will be more convenient.

The expression construct can be joined to a replication system recognized by the intended host cell. Various replication systems include viral replication systems such as retroviruses, simian virus, bovine papilloma virus, or the like In addition, the construct may be joined to an amplifiable gene, e.g., DHFR gene, so that multiple copies of the hPDGF-R gene may be made.

Introduction of the construct into the host will vary depending upon the particular construction. Introduction can be achieved by any convenient means, including fusion, conjugation, transfection, transduction, electroporation, injection, or the like, as amply described in the scientific literature. Introduction of constructs encoding different isoforms of the receptor into a single host cell is also contemplated. The host cells will normally be immortalized cells, that is cells that can be continuously passaged in culture. For the most part, these cells may be any convenient mammalian cell line which is able to express hPDGF-R and where desirable, process the polypeptide so as to provide a mature polypeptide. By processing is intended glycosylation, ubiquitination, disulfide bond formation, or the like. Usually the host will be able to recognize the signal sequence for inserting hPDGF-R into the membrane of the cell. If secretion is desired, the transmembrane locator sequence may be deleted or mutated to prevent membrane insertion of the protein.

A wide variety of hosts may be employed for expression of the peptides, both prokaryotic and eukaryotic. Useful hosts include bacteria, such as *E. coli*, yeast, filamentous fungus, immortalized mammalian cells, such as various mouse lines, monkey lines, Chinese hamster ovary lines, human lines, or the like. For the most part, the mammalian cells will be immortalized cell lines. In some cases, the cells may be isolated from a neoplastic host, or wild-type cells may be transformed with oncogenes, tumor causing viruses, or the like.

Under may circumstances, it will be desirable to transfect mammalian cells which lack a PDGF receptor where the signal sequence directs the peptide into the cell membrane. Lymphocytes and cardiac myocytes are primary cells which lack a receptor. Also, Chinese hamster ovary cells (CHO), epithelial cells lines and a number of human tumor cell lines lack PDGF receptors.

Transfected cells find use as a model for studying cellular responses to PDGF. For controlled investigation, mammalian cells which lack a PDGF receptor can be transfected with an expression construct comprising a DNA sequence encoding hPDGF-R. Cells are produced that encode a receptor that is functionally equivalent to the wild-type receptor and confer a PDGF-sensitive mitogenic response on the cell. In this way, the binding properties of the naturally-occurring PDGF may be analyzed, fragments tested as well as synthetic compounds both proteinaceous and non-proteinaceous. As demonstrated in the Experimental section, transfected cells were used to determine that the AA form of PDGF activates the type B receptor tyrosine kinase. The presence of the type A and type B receptors in a single cell facilitates the study of receptor binding properties.

In addition to studying PDGF-mediated mitogenesis, the transfected cells can be used to evaluate a drug's ability to function as a PDGF agonist or antagonist. In particular, transfected cells can be contacted with the test drug, and the amount of receptor tyrosine kinase activation or the rate of DNA synthesis can be determined in comparison to control cells in the presence or absence of PDGF, or analogs thereof of known activity.

The hPDGF-R protein expressed by transfected cells also finds use. If the peptide is secreted, the peptide may be isolated from the supernatant in which the expression host is grown. If not secreted, the peptide may be isolated from a lysate of the expression host. The peptide may then be isolated by convenient techniques employing HPLC, electrophoresis, gradient centrifugation, affinity chromatography, particularly using PDGF, etc., to provide a substantially pure product, particularly free of cell component contaminants.

The receptor protein or amino acids beginning at about 33 through about 500 of the amino terminal sequence of the receptor which form the external domain, binding portion of the receptor protein find use to affinity purify PDGF. The external domain can also be used affixed to a solid substrate or free in solution to determine drugs useful as PDGF agonists and antagonists.

The protein or the intracellular portion of the protein, beginning at about amino acid 525 through the carboxy terminal amino acid of hPDGF-R, also find use as an enzyme having tyrosine kinase activity. Additionally, amino acids 1 through 32 of the amino terminal sequence of the type B receptor comprise a signal sequence which directs the structural protein through the membrane of a transfected cell. The signal sequence can be used with hPDGF-R, but also finds use with other proteins.

Peptides or portions thereof may also be used for producing antibodies, either polyclonal or monoclonal. Antibodies are produced by immunizing an appropriate vertebrate host, e.g., mouse, with the peptide itself, or in conjunction with a conventional adjuvant. Usually two or more immunizations will be involved, and the blood or spleen will be harvested a few days after the last injection.

For polyclonal antisera, the immunoglobulins may be precipitated, isolated and purified, including affinity purification. For monoclonal antibodies, the splenocytes normally will be fused with an immortalized lymphocyte, e.g., a myeloid line, under selective conditions for hybridomas. The hybridomas may then be cloned under limiting dilution conditions and their supernatants screened for antibodies having the desired specificity. Techniques for producing antibodies are well known in the literature and are exemplified by U.S. Pat. Nos. 4,381,292, 4,451,570 and 4,618,577.

The following examples are offered by way of illustration and not by way of limitation.

EXPERIMENTAL

Screening of Human Kidney λGT11 cDNA Library and Human Placenta λGT10 cDNA Library A full-length DNA sequence encoding the mouse PDGF receptor (mPDGF-R) protein was used as a probe to screen 250,000 plaques of a human kidney cDNA library. Nick translation was used to prepare a probe with specific activity of $12 \times 10^8$ cpm per µg. The filters were incubated with the probe ($10^5$ cpm per ml) in hybridization buffer containing 30% formamide, 1×Denhardt's solution, 5×SC, 0.02M sodium phosphate pH 6.5 and 500 µg per ml of salmon sperm DNA. After 14 hr. of hybridization at 40° C., the filters were washed four times at 55° C. with 0.2×SSC and 0.1% SDS and two additional times at 65° C. with 0.2×SSC. The filters were then air dried and exposed for 16 hrs.

Ten positive clones were obtained which were rescreened with the full-length mPDGF-R probe. Individual clones were isolated and analyzed by restriction analysis using EcoRI endonuclease. The clone containing the largest insert (2.3 kb), designated clone HK-6, was further characterized and sequenced using dideoxy terminators. Clone HK-6 contained the receptor sequence from nucleotide 3554 to nucleotide 5691 plus nine bases from the poly A tail.

A nick-translated probe, prepared from the 2.3 kb HK-6 DNA, was used to screen 250,000 plaques of a human placenta cDNA library. This screening was performed at high hybridization stringency (50% formamide in the hybridization buffer described above). The filters were incubated with $5 \times 10^5$ cpm per ml of probe for 14–16 hrs. at 42° C. The filters were than washed at 65° C. in 0.1% SSC and 0.1% SDS four times.

After secondary screening with the HK-6 probe, seven clones were selected and analyzed by restriction digestion with EcoRI endonuclease. A clone (HP-7) that contained a 4.5 kb insert was selected and characterized. The sequence of that clone is described in FIGS. 1A–1D and encodes the type B human PDGF receptor (B-hPDGF-R).

Construction of Expression Vector

The 4.5 kb DNA fragment containing the complete coding sequence for the type B human PDGF receptor was isolated from the HP-7 clone by EcoRI digestion. The gel purified fragment was cloned into the EcoRI site in the polylinker region of SV40 expression vector PSV7C. The pSV7d expression vector (provided by P. Luciw, University of California, Davis) was a pML derivative containing the SV40 early promoter region (SV40 nucleotides 5190–5270), a synthetic polylinker with restriction sites for EcoRI, SmaI, XbaI, and SalI followed by three translation terminator codons (TAA) and the SV40 polyadenylation signal (SV40 nucleotides 2556–2770) (Truett et al., DNA (1984) 4:333–349). The EcoRI fragment containing the cDNA sequence obtained from the HP-7 clone was inserted at the EcoRI site of the pSV7d. In the resulting expression vector, the B-hPDGF-receptor gene was under transcriptional control of the SV40 promoter.

To ensure the proper orientation of the PDGF receptor insert (4.5 kb) with respect to the SV40 promoter, the positive clones were digested with SmaI endonuclease which cuts at position 573 of the receptor sequence and in the polylinker region of the expression vector.

Clones containing the receptor in the proper transcriptional orientation released a 4.0 kb insert in addition to the 3.2 kb fragment containing the expression vector plus 573 base pairs of the 5' end of the receptor. This plasmid, PSVRH5 was used to co-transfect cells with PSV2 neo plasmid that confers resistance to the antiblotc neomycin.

Cell Culture and Transfection of CHO Cells

CHO cell clone KI, obtained from the U.C.S.F. Tissue Culture Facility, were grown in Ham's F-12 media supplemented with 10% FCS (U.C.S.F. Tissue Culture Facility) and penicillin and streptomycin at 37° C. in 5% $CO_2$/95% air.

pSVRH5 plasmid DNA (10 μu) and pSV2 neo (1 μg) were used to co-transfect 1×10$^6$ CHO cells by the calcium precipitation technique (Van der Eb et al., *Methods Enzymology* (1980) 65:826–839), with the addition of 10 μg chloroquinone diphosphate (CDP) to prevent degradation of the transfected DNA (Luthman and Magnusson, *Nucl. Acid Res.* (1983) 11:1295–1308). After 12 hrs. of exposure to the DNA, the cells were trypsinized and replated at 1:5 dilution. Twenty-four hours later, the antibiotic G418 (GIBCO), an analog of neomycin, was added to the cultures at a concentration of 400 μg/ml.

After two weeks under selection, independent colonies were picked and transferred to 24-well plates. Confluent cultures were assayed for the presence of PDGF receptor by immunoblot using anti-receptor antibodies. Colonies that were positive by this assay were single-cell cloned by end-limiting dilution.

Stable transfected clones were tested for the expression of the type B PDGF receptor message measured by RNA protection assays (Zinn et al., *Cell* (1983) 34:865–879) and for the presence of PDGF-stimulated receptor protein detected by antiphosphotyrosine antibodies (Frackelton et al., *J. Biol. Chem.* (1984) 259:7909–7915).

Expression of B-hPDGF-R cDNA in CHO Cells

CHO cells transfected with plasmid DNA containing the human receptor cDNA under the transcriptional control of the SV40 early promoter (CHO-HR5) and CHO cells transfected with a similar plasmid containing the mouse receptor cDNA (CHO-R18) were solubilized as previously described (Escobedo et al., *J. Biol. Chem.* (1988) 263:1482–1487). Extracts were analyzed by Western blot analysis using an antibody that specifically recognizes sequences in the receptor carboxy-terminal region as previously described in (Escobedo et al., supra; Keating et al., ibid. (1987) 262:7932–7937). The 195 kDa protein is the mature receptor and the 160 kDa protein is the receptor precursor.

The expression of the receptor protein in the transfectants was demonstrated by using antibodies that recognize an intracellular sequence in the receptor. The clone that had the highest level of human receptor expression was chosen for further study. This transfectant had receptors that were labeled with $^{125}$I-PDGF as shown by the competitive binding studies described below.

Competitive Binding of the Different Forms of PDGF to the Type B Receptor

The ability of the human recombinant AA and BB homodimers (Collins et al., *Nature* (1987) 328:621–624) to compete for the type B receptor sites and displace $^{125}$I-labeled PDGF was studied. Each homodimer was produced selectively by a yeast expression system (Brake et al., *Proc. Natl. Acad. Sci. (USA)* (1984) 81:4642–4646) and was purified from yeast media that is devoid of other mesenchymal cell growth factors, thus avoiding the artifact of contamination by factors that might be present in mammalian expression systems.

BALB/c 3T3 cells and CHO transfectants (CHO-HR5) were incubated with $^{125}$I-PDGF (Williams et al., ibid (1982) 79:5067–5070) in the presence of increasing concentrations of AA or BB. Binding was carried out at 37° C. for 45 min. in whole cell suspension. Unbound, radiolabeled PDGF was removed by centrifugation on a Ficoll gradient (Orchansky et al., *J. Immunol.* (1986) 136:169–173). Non-specific binding, determined by incubating CHO cells with $^{125}$I-PDGF, accounted for 25 percent of the bound radioactivity.

The binding study demonstrated that the transfected cells can be used as a model to study the interaction of hPDGF with its receptor. In particular, this study demonstrated that the transfected type B human receptor was functionally identical to the native mouse receptor as indicated by the following results. Both AA and BB forms of PDGF competed for the $^{125}$I-PDGF labeled sites in the human receptor transfectants. For the transfected type B human receptor as well as the native mouse receptor, the BB form was of higher affinity than the AA form. When expressed in yeast, the AA form of PDGF may be processed aberrantly, giving it a lower affinity than the BB form for both the transfected cells and mouse 3T3 cells. The consistency of the pattern of competition shows that the AA form interacts with the transfected type B human receptor in the same way as it does with the native mouse receptor and demonstrates that these receptors are functionally identical.

Activation of the PDGF Receptor Tyrosine Kinase

The ability of recombinant AA and BB homodimers and of human partially purified AB PDGF to activate the type B receptor tyrosine kinase was studied. The yeast-derived AA and BB homodimeric forms and the platelet-derived AB form stimulated autophosphorylation of the transfected human receptor.

BALB/c 3T3 cells and CHO cells transfected with the human PDGF receptor cDNA (CHO-HR5) were incubated with increasing amounts of the different forms of PDGF (AA, BB and AB). Following polyacrylamide-SDS electrophoresis, the phosphorylated receptor was identified by Western blot using an antiphosphotyrosine antibody (Wang, *Mol. Cell. Biol.* (1985) 5:3640–3643).

The receptor protein co-migrated with the 200 kDa molecular weight marker. The concentration of each form that was effective in stimulating autophosphorylation of the transfected human receptor was identical to the concentration that gave a similar autophosphorylation to the native mouse 3T3 receptor or the transfected mouse receptor.

These results showed for the first time that the AA form of PDGF activates the receptor tyrosine kinase of the type B receptor. Prior to use of the transfected cells, there was no demonstration that the AA form had hPDGF activity or that a single receptor, the type B receptor, was capable of recognizing all three forms of PDGF. Further, the results demonstrate that the human cDNA encodes a type B receptor that is functionally equivalent to the wild-type receptor that is responsible for PDGF-stimulated tyrosine kinase activity in mouse 3T3 cells.

Thus, the transfected cells are useful models for studying PDGF-induced mitogenic responses.

Rate of DNA Synthesis in CHO Transfected Cells

BALB/c 3T3 cells and CHO cells transfected with the type B human PDGF receptor cDNA (CHO-HR5) were incubated with saturating concentrations of the three forms of PDGF. Untreated cells and cells treated with fetal calf serum (FCS) were used as negative and positive controls, respectively. The level of $^3$H-thymidine incorporation into DNA was determined by measuring the radioactivity of the acid-precipitable material as previously described (Escobedo, supra).

Transfection of CHO cells with either human type B or mouse PDGF receptor conferred a PDGF-sensitive mitogenic response. All forms of PDGF stimulated DNA synthesis in both the type B human receptor transfectant and the mouse cells bearing the native receptor.

These data showed that the A chain homodimer and the B chain homodimer, like the AB platelet-derived form, were mitogens that can act through the receptor encoded by the type B human cDNA sequence. The mitogenic action of these forms of PDGF on mouse 3T3 cells and CHO cells containing the transfected type B human receptor demonstrate that the responses were mediated by functionally identical receptors.

Isolation and Expression of the Type A PDGF Receptor

The type A receptor was isolated as described for the type B receptor, above, except that different probes were used and hybridization and screening were performed under low stringency conditions, as described below. In particular, a region in the type B receptor tyrosine kinase sequence having a high degree of homology to published tyrosine kinase amino acid sequences was identified and had the amino acid sequence, HRDLAARN. Oligonucleotide probes encoding the tyrosine kinase consensus sequence were prepared having the following sequences:

GTT(G/C)CGXGCXGCCAGXTC(G/C)CGXTG, where G/C indicates either G or C was used and X indicates any of A, T, C or G was used. The human placenta λGT10 cDNA library was screened as described above but with low stringency conditions using a buffer with 6×SSC 0.1% SDS and 5× Denhardt's solution at 42° C. as follows. Filters were screened by washing at 52° C. in 2×SSC. A clone encoding the type A receptor was isolated and sequenced by the procedure described for the type B receptor gene.

The DNA sequence of the gene encoding the type A receptor (A-hPDGF-R) together with the deduced amino acid sequence are shown in FIG. 2A–2E, above.

The clone encoding A-hPDGF-R was digested, gel purified and inserted into the SV40 expression vector, pSV7C, as described for the type B receptor clone.

That vector is used to transfect CHO cells as described above for the type B receptor. With expression of the vector coding sequence, transfected CHO cells produce a functional receptor that binds all three hPDGF isoforms, preferentially binding the AA homodimer.

These studies were made possible by the availability of growth factor preparations devoid of contamination with other growth factors and by the use of a receptor expression system in which all of the measured PDGF responses could be attributed to this single transfected receptor cDNA.

All publications and patent applications herein are incorporated by reference to the same extent as if each individual publication or patent application was specifically and individually indicated to be incorporated by reference. The invention now being full described, it will be apparent to one of ordinary skill in the art that many changes and modifications can be made thereto without departing from the spirit or scope of the appended claims.

What is claimed is:

1. A hPDGF-R fragment having PDGF receptor binding activity, said fragment consisting essentially of amino acids beginning at about 33 through about 500 of the external domain of hPDGF-R.

2. A hPDGF-R fragment having tyrosine kinase activity said fragment consisting essentially of the intracellular portion of a hPDGF-R.

3. A substantially pure preparation of a hPDGF-R fragment of claim 1.

4. The hPDGF-R fragment of claim 1 wherein said fragment is secreted.

5. The hPDGF-R fragment of claim 1, wherein the hPDGF-R is a type A receptor having an amino acid sequence shown in FIGS. 2A–2E.

6. The PDGF-R fragment of claim 1, wherein the PDGF-R is a type B receptor having an amino acid sequence shown in FIGS. 1A–1D.

7. The hPDGF-R fragment of claim 2, wherein the intracellular portion consists essentially of amino acids beginning at about amino acid 525 through the carboxy terminal amino acid of the hPDGF-R.

8. The hPDGF-R fragment of claim 2, wherein the hPDGF-R is a type A receptor having an amino acid sequence shown in FIGS. 2A–2E.

9. The PDGF-R fragment of claim 2, wherein the PDGF-R is a type B receptor having an amino acid sequence shown in FIGS. 1A–1D.

10. A substantially pure preparation of a hPDGF-R fragment of claim 2.

11. A cell producing a hPGDF-R fragment of claim 1.

12. The cell according to claim 11, wherein said cell is a mammalian cell.

13. The cell according to claim 12, wherein said cell lacks an endogenous PDGF receptor.

14. The cell according to claim 13, wherein said cell is a Chinese hamster ovary cell.

15. A cell producing a substantially pure type A hPDGF-R polypeptide comprising an intracellular or extracellular domain of the amino acid sequence shown in FIG. 2 wherein the polypeptide is less than full-length.

16. The cell of claim 15, wherein said cell is a mammalian cell.

17. The cell according to claim 16, wherein said cell lacks an endogenous PDGF receptor.

18. The cell according to claim 17, wherein said mammalian cell is selected from the group consisting of lymphocyte, cardiac myocyte, epithelial cell and Chinese hamster ovary cell.

* * * * *